United States Patent
Ryu et al.

(10) Patent No.: US 10,730,886 B2
(45) Date of Patent: Aug. 4, 2020

(54) COMPOUND HAVING EFFECT OF INHIBITING PLATELET AGGREGATION AND SALT THEREOF, AND COMPOSITION FOR PREVENTING OR TREATING THROMBOTIC DISEASES, CONTAINING SAME

(71) Applicant: SHIN POONG PHARMACEUTICAL CO., LTD., Gyeonggi-do (KR)

(72) Inventors: Jei Man Ryu, Gyeonggi-do (KR); Dong Won Lee, Gyeonggi-do (KR); Kang Hyeok Lee, Gyeonggi-do (KR); Jin Hun Park, Incheon (KR); Geum Sil Cho, Seoul (KR); Ki Sung Lee, Gyeonggi-do (KR); Jin Ho Chung, Seoul (KR); Woo Ile Park, Gyeonggi-do (KR); Jae Young Lee, Gyeonggi-do (KR)

(73) Assignee: Shin Poong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/757,109

(22) PCT Filed: Sep. 2, 2016

(86) PCT No.: PCT/KR2016/009859
§ 371 (c)(1),
(2) Date: Mar. 2, 2018

(87) PCT Pub. No.: WO2017/039395
PCT Pub. Date: Mar. 9, 2017

(65) Prior Publication Data
US 2018/0251472 A1   Sep. 6, 2018

(30) Foreign Application Priority Data
Sep. 4, 2015   (KR) .................. 10-2015-0125270

(51) Int. Cl.
| | | |
|---|---|---|
| *C07D 495/04* | (2006.01) |
| *C07D 261/20* | (2006.01) |
| *C07D 413/04* | (2006.01) |
| *A61K 31/4365* | (2006.01) |
| *A61K 31/5375* | (2006.01) |
| *A61K 31/423* | (2006.01) |
| *A61P 7/02* | (2006.01) |
| *C07C 235/46* | (2006.01) |
| *C07C 235/48* | (2006.01) |
| *C07C 235/56* | (2006.01) |
| *C07D 209/18* | (2006.01) |
| *C07D 213/56* | (2006.01) |
| *C07D 213/66* | (2006.01) |
| *C07D 213/81* | (2006.01) |
| *C07D 231/40* | (2006.01) |
| *C07D 295/073* | (2006.01) |
| *C07D 295/192* | (2006.01) |
| *C07D 309/38* | (2006.01) |
| *C07D 333/24* | (2006.01) |
| *C07D 333/36* | (2006.01) |

(52) U.S. Cl.
CPC .......... *C07D 495/04* (2013.01); *A61K 31/423* (2013.01); *A61K 31/4365* (2013.01); *A61K 31/5375* (2013.01); *A61P 7/02* (2018.01); *C07C 235/46* (2013.01); *C07C 235/48* (2013.01); *C07C 235/56* (2013.01); *C07D 209/18* (2013.01); *C07D 213/56* (2013.01); *C07D 213/66* (2013.01); *C07D 213/81* (2013.01); *C07D 231/40* (2013.01); *C07D 261/20* (2013.01); *C07D 295/073* (2013.01); *C07D 295/192* (2013.01); *C07D 309/38* (2013.01); *C07D 333/24* (2013.01); *C07D 333/36* (2013.01); *C07D 413/04* (2013.01)

(58) Field of Classification Search
CPC ... C07D 495/04; C07D 261/20; C07D 413/04
See application file for complete search history.

(56) References Cited

U.S. PATENT DOCUMENTS

| | | | |
|---|---|---|---|
| 2,899,437 A | 8/1959 | Shapiro et al. | |
| 4,725,598 A | 2/1988 | Takita et al. | |
| 5,244,890 A | 9/1993 | Yamanaka et al. | |
| 8,198,447 B2 * | 6/2012 | Toyooka ............... | C07D 471/04 546/86 |

(Continued)

FOREIGN PATENT DOCUMENTS

| | | | | |
|---|---|---|---|---|
| CA | 2076012 A1 * | 8/1991 | ............. | A61K 31/10 |
| EP | 2412701 A1 | 2/2012 | | |

(Continued)

OTHER PUBLICATIONS

Grant, R., Grant, C. (1987). Grant & Hackh's Chemical Dictionary (5th ed.). New York, NY: McGraw-Hill, p. 313. (Year: 1987).*

(Continued)

*Primary Examiner* — Laura L Stockton

(74) *Attorney, Agent, or Firm* — Harness, Dickey & Pierce, P.L.C.

(57) ABSTRACT

The present invention relates to a novel compound having an effect of inhibiting platelet aggregation and a salt thereof and, more specifically, to: a novel platelet aggregation inhibitor specifically inhibiting shear stress-induced platelet aggregation; a pharmaceutical composition containing the same as an active ingredient; and a preparation method therefor.

8 Claims, No Drawings

(56) References Cited

U.S. PATENT DOCUMENTS

| | | | | |
|---|---|---|---|---|
| 8,575,127 | B2 * | 11/2013 | Yanachkov | C07D 473/24 514/46 |
| 2011/0294790 | A1 | 12/2011 | Mantegani et al. | |
| 2013/0196050 | A1 * | 8/2013 | Amino | C07C 233/51 426/650 |

FOREIGN PATENT DOCUMENTS

| | | | | |
|---|---|---|---|---|
| WO | WO-2012/025638 A1 * | 3/2012 | | C07D 277/24 |
| WO | WO-2013/087834 A2 | 6/2013 | | |
| WO | WO-2014070983 A1 | 5/2014 | | |
| WO | WO-2014/118361 A1 * | 8/2014 | | A61K 31/16 |

OTHER PUBLICATIONS

Chemical Abstracts Registry No. 1916209-57-8, indexed in the Registry file on STN CAS Online May 23, 2016. (Year: 2016).*

Chemical Abstracts Registry No. 1789695-91-5, indexed in the Registry file on STN CAS Online Jun. 26, 2015 (Year: 2015).*

Chemical Abstracts Registry No. 14443-30-2, indexed in the Registry file on STN CAS Online Nov. 16, 1984. (Year: 1984).*

Liechti, Chemical Abstracts 157:519584, 2012. (Year: 2012).*

Kim et al., Biochemical Pharmacology, 86, 2013, pp. 1747-1761. (Year: 2013).*

Chapado, L., et al.; Synthesis and Evaluation of the Platelet Antiaggregant Properties of Phenolic Antioxidants Structurally Related to Rosmarinic Acid, Bioorganic Chemistry, Date of E-publication Dec. 5, 2009, vol. 38, pp. 108-114.

Li, G., et al., "Lingustrazinyl Amides: a Novel Class of Ligustrazine Phenolic Acid Derivatives with Neuroproective Effects", Chemistry Central Journal, Date of E-publication Mar. 4, 2015, vol. 9, Paper No. 9.

International Search Report from corresponding International Application No. PCT/KR2016/009859 dated Dec. 8, 2016, and it's English translation.

Park, J. B., et al.; "Becatamide Found in Houttuynia Cordata Suppresses P-Selectin Via Inhibiting Cox Enzyme, Not Increasing Camp in Platelets", Phytotherapy Research, 29, 2015, pp. 1381-1387.

St. John, S. E., et al.; "Design, Synthesis, Biological and Structural Evaluation of Functionalized Resveratrol Analogues As Inhibitors of Quinone Reductase 2", Bioorganic & Medicinal Chemistry 21 (2013) 6022-6037.

Marzaro, G., et al.; "Using the Tops-Mode Approach to Fit Multi-Target QSAR Models for Tyrosine Kinases Inhibitors", European Journal of Medicinal Chemistry 46 (2011) 2185-2192.

Sun, L.M., et al.; "Alkaloids From Aconitum Barbatum Var. Puberulum", Helvetica Chimica Acta—vol. 92 (2009), pp. 1126-1133.

Yu, K. L.. et al.; "Novel Quinolizidine Salicylamide Influenza Fusion Inhibitors", Bioorganic & Medicinal Chemistry Letters 9 (1999) 2177-2180.

Ford, R. E., et al.; "Synthesis and Quantitative Structure-Activity Relationships of Antiallergic 2-Hydroxy-IV-LJI-Tetrazol-5-Ylbenzamides and IV-(2-Hydroxyphenyl)-LII-Tetrazole-5-Carboxamides", J. Med. Chem. 1986, 29, 538-549.

Schubert, V. H., et. al.; "Synthese Und Oxydation Von Unsymmetrisch Verbrückten Dihydrochinonen", Journal F, Prakt. Chemie. Band 319. Heit 5, 1977, S. 745-794.

Extended European Search Report From Corresponding European Patent Application No. 16842361.4, dated Aug. 9, 2019.

* cited by examiner

COMPOUND HAVING EFFECT OF INHIBITING PLATELET AGGREGATION AND SALT THEREOF, AND COMPOSITION FOR PREVENTING OR TREATING THROMBOTIC DISEASES, CONTAINING SAME

This application is a national phase application of PCT Application No. PCT/KR2016/009859, filed on 2 Sep. 2016, which claims the benefit of Korean Patent Application No. 10-2015-0125270 filed 4 Sep. 2015.

FIELD

The present invention relates to a new compound having inhibitory effect for platelet aggregation and a salt thereof. More specifically, the present invention relates to a new platelet aggregation inhibitor that can selectively inhibit shear stress-induced platelet aggregation; a pharmaceutical composition comprising the same as an active ingredient; and a process for preparing the same.

BACKGROUND

The human body has a self-healing or defensive system for healing and prevention of loss of blood at wound sites, which is achieved by modulation and balancing among clotting of platelets and plasma, degradation of fibrin, and inhibition of coagulation. When these proper control and balance are disturbed by various factors, abnormal platelet aggregation occurs and that leads to thrombotic diseases.

Thrombosis refers to a condition wherein the blood circulation system is disturbed by a blood clot in the blood vessel, or in the worst case, the flow of blood is blocked. Thrombosis may cause atherothrombosis, phlebothrombosis, hepatic portal vein thrombosis, pulmonary thromboembolism, chronic limb ischemia, varicose veins, deep vein thrombosis diseases, angina pectoris, cerebral infarction, cerebral hemorrhage, and the like, and it may also contribute to infection, vascular injury, postoperative complications, coagulative diseases, and the like. Such thrombosis can be generated by interaction among abnormal blood vessel walls, hemodynamic forces, coagulation proteins in the plasma, and platelets. Platelets are activated by various agonists such as adenosine diphosphate, thromboxane $A_2$, and thrombin, and the activated platelet glycoproteins such as IIb/IIIa are combined with aggregation proteins in the blood (fibrinogen, von Willebrand factor, etc.) to cause an aggregation reaction.

Recently, it has been known that platelets are abnormally activated not only by chemical agonists but also by physical stimulation, resulting in thrombosis. Among the physical stimuli, shear stress is the most influential factor in platelet activation. Shear stress refers to the force of the bloodstream on the cells within the blood vessels, such as platelets, red blood cells and endothelial cells. An abnormal change in shear stress is the major cause of pathologic arterial thromboli development in vivo, which is caused by artery dissection due to percutaneous coronary intervention such as stent, atherectomy, and balloon angioplasty; vascular spasm; or diseases such as hypertension and atherosclerosis.

When the shear stress increases abnormally, platelets are activated, and the glycoproteins IIb/IIIa of the activated platelets directly bind to von Willebrand factor, resulting in aggregation. These phenomena accelerate the signaling pathway in platelets, increase intracellular calcium concentration, and induce the release of various activating factors from granules, thereby promoting platelet aggregation and producing thrombosis (Nesbitt et al., Nature Medicine 15, 665-673 (2009)).

The currently used agents for the prevention and treatment of thrombotic diseases include antiplatelet agents that antagonize chemical agonists (e.g., aspirin, clopidogrel, etc.), anticoagulants (e.g., heparin, warfarin, etc.), thrombolytic agents for treating preformed thrombli (e.g., tissue plasminogen activator, etc.), and so on. Aspirin is known to cause side effects such as gastrointestinal bleeding and peptic ulcer, although it is fairly effective. Most of the other anticoagulants cannot be orally administered and exhibit various side effects after prolonged administration such as hemorrhage, hemolysis, immune reaction, fever and allergy, because of their low selectivity for thrombosis. In addition to these side effects and ineffectiveness, there is another problem of prohibitively expensive prices of some commercially available therapeutic agents.

For the above reasons, there is a need to develop an antiplatelet agent that selectively affects shear stress-induced platelet aggregation and has few side effects (Kiefer and Becker, Circulation, 2009, 120:2488-2495/Gilbert et al., Circulation, 2007, 116:2678-2686).

DISCLOSURE OF THE INVENTION

Problem to be Solved

The present invention is based on the finding that certain compounds having amide and ester structures that are obtained through the structure activity relationship study of platelet aggregation inhibition are useful for prevention or treatment of thrombotic diseases while having few side effects such as bleeding.

Means to Solve the Problem

One aspect of the present invention relates to a compound represented by the following Formula (I) or (II), or a pharmaceutically acceptable salt or isomer thereof:

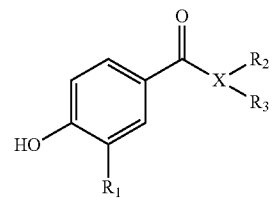

[Formula I]

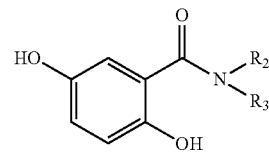

[Formula II]

wherein, $R^1$ is hydroxy or $C_1$-$C_{10}$ alkoxy;

X is N or O;

$R^2$ is —$(CH_2)_p$-5- to 12-membered heterocycle-$(CH_2)_p$— $C_6$-$C_{12}$ aryl, 5- to 12-membered heterocycle, —$(CH_2)_p$— NHC(=O)—$C_6$-$C_{12}$ aryl, —$CHR^4R^5$, 5- to 12-membered heteroaryl, $C_6$-$C_{12}$ aryl, —$C_6$-$C_{12}$ aryl-O-5- to 12-membered heteroaryl, —$(CH_2)_p$-5- to 12-membered heteroaryl, or —$(CH_2)_p$—$C_6$-$C_{12}$ aryl, wherein p is an integer of 1 to 10; $R^4$ and $R^5$ are each independently $C_1$-$C_6$ alkoxycarbonyl or —$CH_2$-5- to 12-membered heteroaryl; said heterocycle and heteroaryl may contain 1 to 3 heteroatoms selected from N, O, and S; and said heterocycle, heteroaryl, and aryl can be substituted with 1 to 4 substituents selected from the group consisting of halogen, oxo, aminocarbonyl, $C_1$-$C_6$ alkyl, nitro, $C_1$-$C_6$ alkoxy, nitrile, $C_1$-$C_6$ alkylaminocarbonyl, hydroxy, and hydroxy-$C_1$-$C_6$ alkyl;

$R^3$ is hydrogen;

when X is O, $R^3$ does not exist;

when X is N, X taken together with $R^2$ and $R^3$ may form a 5- to 12-membered heterocycle containing 1 to 3 heteroatoms selected from O, N and S; wherein said heterocycle can be substituted with $C_6$-$C_{12}$ aryl; a 6- to 12-membered heteroaryl containing 1 to 3 heteroatoms selected from O, N and S, which is unsubstituted or substituted with halogen; or —O—$CHR^6R^7$; and wherein $R^6$ and $R^7$ are each independently $C_6$-$C_{12}$ aryl or a 6- to 10-membered heteroaryl containing 1 to 3 heteroatoms selected from N, O and S, both of which are unsubstituted or substituted with halogen.

Specific examples of the compounds are as follows:
1. (6,7-Dihydrothieno[3,2-c]pyridin-5(4H)-yl)(3,4-dihydroxyphenyl)methanone
2. (3,4-Dihydroxyphenyl)(4-(5-fluorobenzo[d]isoxazol-3-yl)piperidin-1-yl)methanone
3. N-((4-(4-Fluorobenzyl)morpholin-2-yl)methyl)-3,4-dihydroxybenzamide
4. 3,4-Dihydroxy-N-(2-oxotetrahydrothiophen-3-yl)benzamide
5. N,N'-(Nonan-1,9-diyl)bis(3,4-dihydroxybenzamide)
6. (4-((4-Chlorophenyl)(pyridin-2-yl)methoxy)piperidin-1-yl)(3,4-dihydroxyphenyl)methanone
7. (S)-(4-((4-Chlorophenyl)(pyridin-2-yl)methoxy)piperidin-1-yl)(3,4-dihydroxyphenyl)methanone
8. (S)-Methyl-2-(3,4-dihydroxybenzamido)-3-(1H-indol-3-yl)propanoate
9. 4-(3,4-Dihydroxybenzamido)-1-methyl-3-propyl-1H-pyrazole-5-carboxamide
10. 2-Methyl-4-oxo-4H-pyran-3-yl 3,4-dihydroxybenzoate
11. (3,4-Dihydroxyphenyl)(4-phenylpiperazin-1-yl)methanone
12. (6,7-Dihydrothieno[3,2-c]pyridin-5(4H)-yl)(4-hydroxy-3-methoxyphenyl)methanone
13. 2-Ethyl-4-oxo-4H-pyran-3-yl 4-hydroxy-3-methoxybenzoate
14. 2-Methyl-4-oxo-4H-pyran-3-yl 4-hydroxy-3-methoxybenzoate
15. 4-Hydroxy-3-methoxy-N-(4-methoxy-2-nitrophenyl)benzamide
16. N-(3-Ethynylphenyl)-4-hydroxy-3-methoxybenzamide
17. 4-(4-(4-Hydroxy-3-methoxybenzamido)phenoxy)-N-methylpicolinamide
18. 4-((4-Chlorophenyl)(pyridin-2-yl)methoxy)piperidin-1-yl)(4-hydroxy-3-methoxyphenyl)methanone
19. 4-Hydroxy-N-((3-hydroxy-5-(hydroxymethyl)-2-methylpyridin-4-yl)methyl)-3-methoxybenzamide
20. (6,7-Dihydrothieno[3,2-c]pyridin-5(4H)-yl)(2,5-dihydroxyphenyl)methanone
21. (4-((4-Chlorophenyl)(pyridin-2-yl)methoxy)piperidin-1-yl)(2,5-dihydroxyphenyl)methanone
22. N-((4-(4-Fluorobenzyl)morpholin-2-yl)methyl)-2,5-dihydroxybenzamide
23. (2,5-Dihydroxyphenyl)(4-(5-fluorobenzo[d]isoxazol-3-yl)piperidin-1-yl)methanone
24. N-(3,4-Dimethoxyphenethyl)-2,5-dihydroxybenzamide
25. 2,5-Dihydroxy-N-(2-(thiophen-2-yl)ethyl)benzamide
26. 2,5-Dihydroxy-N-(2-oxotetrahydrothiophen-3-yl)benzamide.

Thus, another aspect of the present invention relates to a compound that is individually selected from the above group, or a pharmaceutically acceptable salt or isomer thereof.

Yet another aspect of the present invention relates to a composition for the prevention or treatment of thrombotic diseases due to platelet aggregation, comprising as an active ingredient a compound of Formula (I) or (II), or a pharmaceutically acceptable salt or isomer thereof. Thrombotic diseases as referred to herein may include, but are not limited to, for example, pulmonary embolism, thrombotic phlebitis, deep vein thrombosis, portal thrombosis, angina pectoris, arteriosclerosis, or cerebral infarction.

The pharmaceutical composition according to the present invention may be formulated in a suitable form together with a conventionally used pharmaceutically acceptable carrier (s). The term "pharmaceutically acceptable" refers to an ingredient that is physiologically acceptable and that generally does not cause an allergic reaction such as gastrointestinal disorder and dizziness, or a similar reaction, when administered to humans. Examples of such pharmaceutically acceptable carriers include carriers such as water, suitable oils, saline, aqueous glucose, and glycols for parenteral administration.

In addition, the composition according to the present invention may further comprise a stabilizer and a preservative. Suitable stabilizers may include antioxidants such as sodium bisulfite, sodium sulfite and ascorbic acid. Suitable preservatives may include benzalkonium chloride, methyl- or propyl-paraben and chlorobutanol. In addition, the composition according to the present invention may properly comprise suspending agents, solubilizing agents, stabilizers, tonicity agents, preservatives, anti-adherents, surfactants, diluents, excipients, pH-adjusting agents, pain-relieving agents for injection pain, buffering agents, antioxidants, and the like, if needed depending on administration routes and dosage forms. Pharmaceutically acceptable carriers and formulations suitable for the present invention, including those exemplified above, are described in detail in the literature [Remington's Pharmaceutical Sciences, Current Edition]. The compositions of the present invention may be prepared in unit dosage form or may be prepared by incorporation into a multi-dose container. In the pharmaceutical composition, the compounds of the present invention are present in an amount of 0.0001 to 10% by weight, preferably 0.001 to 1% by weight, based on the total weight of the total composition.

The administration method of the pharmaceutical composition of the present invention can be easily selected depending on the type of formulation and can be administered to mammals such as livestocks and humans in various routes, in the following oral or parenteral administration forms.

Examples of formulations for oral administration include tablets, pills, hard/soft capsules, liquids, suspensions, emulsions, syrups, granules, elixirs, troches and the like. These formulations may contain, in addition to the active ingredient, diluents (for example, lactose, dextrose, sucrose, mannitol, sorbitol, cellulose, and/or glycine) and lubricants (for example, silica, talc, stearic acid, and magnesium or calcium salt thereof, and/or polyethylene glycol). The tablets may also contain binders such as magnesium aluminum silicate, starch paste, gelatin, methyl cellulose, sodium carboxymethyl cellulose and/or polyvinyl pyrrolidine, and may optionally contain disintegrants thereof such as starch, agar, alginic acid or its sodium salt; or effervescent mixtures and/or absorbents, colorants, flavors and sweeteners.

Formulations for parenteral administration include sterile aqueous solutions, non-aqueous solutions, suspensions, emulsions, freeze-dried (lyophilized) preparations and suppositories. Propylene glycol, polyethylene glycol, vegetable oil such as olive oil, injectable ester such as ethyl oleate and the like may be used for the non-aqueous solutions and suspensions. Witepsol, macrogol, tween 61, cacao butter, sevum laurin, glycerol, gelatin and the like may be used as a base for suppositories. In order to prepare the formulation for parenteral administration, the compounds of Formula (I) or (II) or a pharmaceutically acceptable salt thereof may be sterilized and/or mixed in water with additives such as preservatives, stabilizers, hydrating agents or emulsifying accelerators, salts and/or buffers for adjusting osmotic pressure, and other therapeutically useful substances to prepare solutions or suspensions, which may be prepared in ampoules or vial unit dosage forms.

Preferable doses for the human body of the pharmaceutical composition of the present invention that comprises the compounds of Formula (I) or (II) as an active ingredient will vary depending on the condition and weight of the patient, the degree of disease, the type of drug, the route of administration, and the treatment duration, but can be appropriately selected by those skilled in the art. Preferably, however, the compounds of the present invention can be administered at a daily dose of 0.001 to 100 mg/kg body weight, more preferably 0.01 to 30 mg/kg body weight. The administration may be carried out once a day or divided into several times a day. The doses may vary depending on various conditions such as the patient's body weight, age, sex, health condition, diet, time of administration, administration method, excretion rate and severity of disease, and thus it will be apparent to those skilled in the art that the doses may be additive or subtractive. Therefore, the above doses do not in any way limit the scope of the invention. The number of administrations may be once a day or several times a day within a desired range, and the administration period is not particularly limited.

The compounds represented by Formula (I) or (II) as described above activate platelet aggregation inhibition.

Shear stress is a physical stimulus applied to blood cells such as platelets and red blood cells and to vascular endothelium by blood flow. In normal conditions, it is maintained at a low level of 300 to 1500 $s^{-1}$, but it increases abnormally and even increases to 10,000 $s^{-1}$ or more when the blood vessels are narrowed for pathological reasons such as stenosis, arteriosclerosis, cancer, and vasospasm. This excessively elevated shear stress can directly activate and aggregate platelets, whose condition is defined as shear stress-induced platelet aggregation (SIPA). Shear stress-induced platelet aggregation is initiated by the binding of von Willebrand factor (vWF) with glycoprotein (GP) Ib, and is followed by increased intracellular calcium concentration, secretion of active factors from the granule, and expression of adherent proteins, which lead to stable platelet aggregation and thrombogenesis.

Practically, shear stress is one of the most important causes of pathologic arterial thrombosis in vivo, but to date no drug has been developed or is under development that targets shear stress-induced platelet aggregation. Hence, the development of such a drug will be a first-in-class and it is expected to pave the way for new markets as well as replacing existing products. Particularly, unlike other chemical agonists, this drug induces platelet activation through a novel mechanism and is advantageous in reflecting the in vivo environment caused by changes in blood flow, and it is expected that its mechanism of action is subdivided into 5 steps of vWF-GP Ib binding, intracellular $Ca^{2+}$ change, GP IIb/IIIa activation, vWF secretion, and ADAMTS13 activation.

In addition, the compounds represented by Formula (I) or (II) of the present invention show almost no side effects such as bleeding even when taken for a long time, unlike the conventional antiplatelet agents.

As used herein, the term "prevention (preventing)" refers to any act that inhibits or delays the onset of a related disease upon administration of the composition according to the invention. It will be apparent to those skilled in the art that the composition of the present invention can prevent such a disease when administered before or in the early stage of the onset of symptoms.

As used herein, the term "treatment (treating)" refers to any act that improves or changes into an advantageous state the symptoms of a related disease upon administration of the composition according to the present invention, and it includes alleviation and improvement. Any person having ordinary skill in the art will be able to know the precise criteria of the disease and can judge the degree of alleviation, improvement and treatment of the disease by referring to the data presented by the Korean Medical Association, etc.

Yet another aspect of the present invention relates to a method for treating or preventing thrombosis comprising administering a therapeutically effective amount of the composition according to the present invention to a subject in need of treatment of thrombosis.

The term "subject" as used herein refers to a subject in need of treatment of a disease, and more specifically refers to mammals including humans, non-human primates, mice, rats, dogs, cats, horses and cows.

The method of administering the composition according to the present invention to a subject can be carried out as described above.

The term "therapeutically effective amount" as used herein refers to an amount of the compounds according to the present invention or the pharmaceutical composition comprising said compounds that is sufficient to treat, inhibit, alleviate or prevent thrombosis as described above, which may be determined by conducting a benefit/risk ratio determination that is applied to any drug. However, the total daily dose may be determined by the physician's reasonable opinion. In addition, the daily dose of a particular patient may also be determined by considering a variety of factors known in the art, such as, for example, the type of specific disease, the severity of the disease, the type of the particular drug administered, the type of composition used, the patient's age, body weight, general health condition, sex, diet, the time of administration, the route of administration, the absorption, distribution and excretion rate of the drug, the duration of the administration, the type of other drug used, and the like. Furthermore, at the initial stage of drug administration, a drug is administered in an amount less than that required for the desired effect, and the dose is gradually increased until the desired effect is obtained.

Effect of the Invention

The compounds according to the present invention, or pharmaceutically acceptable salts or isomers thereof, have an effect of inhibiting platelet aggregation, and the composition comprising the same can efficiently prevent or treat a thrombotic disease with few side effects such as bleeding.

SPECIFIC EMBODIMENTS OF THE INVENTION

Hereinafter, in order to facilitate understanding of the present invention, examples will be presented. However, the following examples are provided only for the purpose of easier understanding of the present invention, and the present invention is not limited to the following examples,

EXAMPLES

Preparation of Experiments and Instruments
1. Analytical Instruments

The following instruments were used to identify the structure of the product obtained in this experiment. The nuclear magnetic resonance spectrum (1H-NMR) was used with 300 MHz or 400 MHz, and the solvents were $CDCl_3$ and DMSO-d6. The coupling constant (J) was expressed in Hz. The mass spectrum (manufacturer: JEOL/model name: JMS-AX 505 wA spectrometer; or manufacturer: JEOL/model name: JMS-HX/HX 110A spectrometer) was used according to the manufacturer's manual and expressed in m/z form.

2. TLC and Column Chromatography

Silica gel (Merck F254) from Merck was used for thin layer chromatography (TLC) and silica (Merck EM 9385, 230-400 mesh) was used for column chromatography. In addition, to confirm the separated substances on TLC, the plate was monitored under UV lamp (at 254 nm), or the plate was immersed in anisaldehyde and potassium permanganate ($KMnO_4$) color development reagents, followed by heating.

3. Reagents Used

The reagents used in this experiment were purchased from Sigma-Aldrich, Lancaster, or Fluka, and the solvents used in the reaction were purchased from Sigma-Aldrich, Merck or Junsei Chemical Co. (Japan). The first grade reagents were used without purification. THF used as the solvent was prepared by heating under reflux over sodium metal in the presence of benzophenone in an argon stream until it turned blue. Dichloromethane ($CH_2Cl_2$) was prepared by adding $CaH_2$ in an argon stream and heating under reflux. Ethyl acetate and hexane were heated under reflux in an argon stream and purified.

Preparation Example 1: Preparation of 3,4-Diacetoxybenzoic Acid 10.0 g of PCA was added to a mixture of 150 mL of purified water and 36.1 mL of TEA, and 18.4 mL of acetic anhydride was added dropwise at 20° C. or lower. The mixture was stirred at room temperature overnight. Hydrochloric acid was added thereto to adjust the pH to 3.0, and the mixture was stirred at room temperature for 1 hour. The resulting solid was filtered, washed with purified water, and dried at 40° C. to obtain 9.2 g of the title compound as a white solid.

Yield: 59.5%

$^1$H NMR (400 MHz, $CDCl_3$) δ 8.05 (dd, J=2.0 and 8.4 Hz, 1H), 7.97 (d, J=2.0 Hz, 1H), 7.35 (d, J=8.8 Hz, 1H), 2.35 (s, 3H), 2.34 (s, 3H)

Preparation Example 2: Preparation of 4-Acetoxy-3-methoxybenzoic Acid

Vanillic acid (10.0 g) was added to a mixture of 150 mL of purified water and 16.5 mL of TEA, and 8.4 mL of acetic anhydride was added dropwise at 20° C. or lower. The mixture was stirred at room temperature overnight. Hydrochloric acid was added thereto to adjust the pH to 3.0, and the mixture was stirred at room temperature for 1 hour. The resulting solid was filtered, washed with purified water and dried at 40° C. to obtain 10.7 g of the title compound as an ocher-colored solid.

Yield: 85.5%

$^1$H NMR (400 MHz, $CDCl_3$) δ 7.78 (dd, J=6.4 and 8.0 Hz, 1H), 7.73 (d, J=2.0 Hz, 1H), 7.16 (d, J=8.4 Hz, 1H), 3.93 (s, 3H), 2.37 (s, 3H)

Example 1: (6,7-Dihydrothieno[3,2-c]pyridin-5(4H)-yl)(3,4-dihydroxyphenyl)methanone 0.5 g of 3,4-diacetoxybenzoic acid obtained in Preparation Example 1 was added to DCM 10 mL, and the mixture was stirred at 10° C. 0.66 g of $PCl_5$ was added at 10° C. or lower, the mixture was stirred for 2 hours while maintaining the temperature at 0 to 10° C., and 10 ml of purified water was added for extraction. The aqueous layer was discarded, and the organic layer was dried over $Na_2SO_4$ and filtered. The filtrate was concentrated, 10 mL of DCM was added, cooled to 0° C., and 0.33 g of 4,5,6,7-tetrahydrothieno[3,2,c]pyridine hydrochloride was added. 0.44 mL of TEA was added dropwise while maintaining the temperature at 0° C., the temperature was gradually raised to room temperature, and the mixture was stirred for 2 hours. DCM phase was concentrated and 10 mL of EtOAC and 10 mL of purified water were added for layer separation. The aqueous layer was further extracted with 10 mL of EtOAc, the residual aqueous layer was discarded, and the organic layer was concentrated. 5 mL of MeOH, 5 mL of purified water and 2.9 mL of TEA were added to the concentrate, and the mixture was refluxed for 4 hours. The MeOH phase was concentrated, 10 mL of EtOAc and 10 mL of purified water were added, and the layers were separated. The organic layer was concentrated, and sonicated for 5 minutes after the addition of a small amount of DCM. The resulting solid was filtered and washed with a small amount of DCM to obtain 0.38 g of the title compound as a white solid.

Yield: 65.7%

$^1$H NMR (400 MHz, DMSO-$d_6$) δ 9.30 (brs, 2H), 7.35 (d, J=4.0 Hz, 1H), 6.88 (brs, 1H), 6.84 (s, 1H), 6.77 (d, J=4.0 Hz, 1H), 4.64 (s, 1H), 3.96 (s, 1H), 3.87 (s, 1H), 2.89 (s, 1H), 2.81 (s, 1H)

Example 2: (3,4-Dihydroxyphenyl)(4-(5-fluorobenzo[d]isoxazol-3-yl)piperidin-1-yl)methanone 0.5 g of 3,4-diacetoxybenzoic acid obtained in Preparation Example 1 was added to DCM 10 mL, and the mixture was stirred at 10° C. 0.66 g of $PCl_5$ was added at 10° C. or lower, the mixture was stirred for 2 hours while maintaining the temperature at 0 to 10° C., and 10 ml of purified water was added to extraction. The aqueous layer was discarded and the organic layer was dried over $Na_2SO_4$ and filtered. The filtrate was concentrated, 10 mL of DCM was added, cooled to 0° C., and 0.48 g of 6-fluoro-3-(4-piperidinyl)-1,2-benzisoxazole hydrochloride was added. 0.44 mL of TEA was added dropwise while maintaining the temperature at 0° C., the temperature was gradually raised to room temperature, and the mixture was stirred for 2 hours, DCM phase was concentrated, and 10 mL of EtOAC and 10 mL of purified water were added for extraction. The aqueous layer was further extracted with 10 mL of EtOAc, the residual aqueous layer was discarded, and the organic layer was concentrated. 5 mL of MeOH, 5 mL of purified water and 2.9 mL of TEA were added to the concentrate, and the mixture was refluxed for 4 hours. The MeOH phase was concentrated, 10 mL of EtOAc and 10 mL of purified water were added, and the layers were separated. The organic layer was concentrated and sonicated for 5 mines after the addition of a small amount of DCM. The resulting solid was filtered and washed with a small amount of DCM to obtain 0.42 g of the title compound as a white solid.

Yield: 56.1%

$^1$H NMR (400 MHz, DMSO-d$_6$) δ 9.23 (brs, 2H), 8.07 (dd, J=5.6 and 8.8 Hz, 1H), 7.71 (dd, J=2.0 and 9.2 Hz, 1H), 7.30 (td, J=2.0 and 9.2 Hz, 1H), 6.84 (d, J=1.6 Hz, 1H), 6.76~6.75 (m, 2H), 4.19 (brs, 2H), 3.53~3.46 (m, 2H), 3.12 (brs, 1H), 2.10~2.07 (m, 2H), 1.83~1.73 (m, 1H)

Example 3: N-((4-(4-Fluorobenzyl)morpholin-2-yl)methyl)-3,4-dihydroxybenzamide 3.0 g of 3,4-diacetoxybenzoic acid obtained in Preparation Example 1 was added to DCM 60 mL, and the mixture was stirred at 10° C. 3.9 g of PCl$_5$ was added at 10° C. or lower, the mixture was stirred for 2 hours while maintaining the temperature at 0 to 10° C., and 60 ml of purified water was added for layer separation. The aqueous layer was discarded and the organic layer was dried over Na$_2$SO$_4$ and filtered. The filtrate was concentrated, added with 60 mL of DCM, cooled to 0° C., and 2.7 g of 3-aminomethyl-4-(4-fluorobenzyl)morpholine was added. 5.2 mL of TEA was added dropwise while maintaining the temperature at 0° C., the temperature was gradually raised to room temperature, and the mixture was stirred for 2 hours. DCM phase was concentrated and 60 mL of EtOAC and 60 mL of purified water were added for extraction. The aqueous layer was further extracted with 60 mL of EtOAc, the aqueous residual layer was discarded, and the organic layer was concentrated. 3 mL of MeOH, 3 mL of purified water and 17.5 mL of TEA were added to the concentrate, and the mixture was refluxed for 4 hours. The MeOH phase was concentrated and 60 mL of EtOAc and 60 mL of purified water were added for extraction. The organic layer was concentrated, purified by flash column chromatography, and vacuum-dried to obtain 2.9 g of the title compound as a foam.

Yield: 63.8%

$^1$H NMR (400 MHz, DMSO-d$_6$) δ 9.45 (brs, 1H), 9.11 (brs, 1H), 8.18 (t, J=5.6 Hz, 1H), 7.33 (dd, J=5.6 and 8.4 Hz, 2H), 7.27 (d, J=1.6 Hz, 1H), 7.19~7.11 (m, 3H), 6.75 (d, J=8.4 Hz, 1H), 3.77 (d, J=10.8 Hz, 1H), 3.59~3.40 (m, 4H), 3.29~3.17 (m, 2H), 2.73 (d, J=11.2 Hz, 1H), 2.55 (d, J=11.2 Hz, 1H), 2.04 (t, J=10.4 Hz, 1H), 1.82 (d, J=10.4 Hz, 1H)

Example 4: 3,4-Dihydroxy-N-(2-oxotetrahydrothiophen-3-yl)benzamide

To 10 mL of DMF were added 0.5 g of protocatechuic acid, 0.68 g of EDC, 0.48 g of HOBt, 1.4 mL of TEA and 0.55 g of homosystein thiolactone hydrochloride, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over Na$_2$SO$_4$, and filtered. The filtrate was concentrated by distillation under reduced pressure and purified by flash column chromatography to obtain 0.28 g of the title compound as a white solid.

Yield: 34.1%

$^1$H NMR (400 MHz, DMSO-d$_6$) 9.52 (brs, 1H), 9.17 (brs, 1H), 8.42 (d, J=8.0, 1H), 7.29 (d, J=2.0, 1H), 7.20 (dd, J=2.0 and 8.4, 1H), 6.77 (d, J=8.8, 1H), 4.79 (sex, J=7.6, 1H), 3.47~3.29 (m, 2H), 2.46~2.22 (m, 2H)

Example 5: N,N'-(Nonan-1,9-diyl)bis(3,4-dihydroxybenzamide)

0.5 g of 3,4-diacetoxybenzoic acid obtained in Preparation Example 1 was added to DCM 10 mL, and the mixture was stirred at 10° C. 0.66 g of PCl$_5$ was added at 10° C. or lower, the mixture was stirred for 2 hours while maintaining the temperature at 0 to 10° C., and 10 ml of purified water was added for layer separation. The aqueous layer was discarded and the organic layer was dried over Na$_2$SO$_4$ and filtered. The filtrate was concentrated, added with 10 mL of DCM, cooled to 0° C., and 0.13 g of 1,9-diaminononane was added. 0.44 mL of TEA was added dropwise while maintaining the temperature at 0° C., the temperature was gradually raised to room temperature, and the mixture was stirred for 2 hours. DCM was concentrated and 10 mL of EtOAC and 10 mL of purified water were added for layer separation. The aqueous layer was extracted with 10 mL of EtOAc, the aqueous layer was discarded, and the organic layer was concentrated. 5 mL of MeOH, 5 mL of purified water and 2.9 mL of TEA were added to the concentrate, and the mixture was refluxed for 4 hours. The MeOH solution was concentrated, 10 mL of EtOAc and 10 mL of purified water were added, and the layers were separated. The organic layer was concentrated under reduced pressure and purified by flash column chromatography to obtain 0.65 g of the title compound as a white solid.

Yield: 71.9%

$^1$H NMR (400 MHz, DMSO-d$_6$) δ 9.40 (brs, 2H), 9.08 (brs, 2H), 8.10 (t, J=5.6 Hz, 2H), 7.26 (d, J=2.4 Hz, 2H), 7.17 (dd, J=2.0 and 8.0 Hz, 2H), 6.74 (d, J=8.0 Hz, 2H), 3.09 (q, J=6.8 Hz, 4H), 1.47 (t, J=6.0 Hz, 4H), 1.27 (s, 10H)

Example 6: (4-((4-Chlorophenyl)(pyridin-2-yl)methoxy)piperidin-1-yl)(3,4-dihydroxyphenyl)methanone 0.5 g of 3,4-diacetoxybenzoic acid obtained in Preparation Example 1 was added to DCM 10 mL, and the mixture was stirred at 10° C. 0.66 g of PCl$_5$ was added at 10° C. or lower, the mixture was stirred for 2 hours while maintaining the temperature at 0 to 10° C., and 10 ml of purified water was added for layer separation. The aqueous layer was discarded and the organic layer was dried over Na$_2$SO$_4$ and filtered. The filtrate was concentrated, added with 10 mL of DCM, cooled to 0° C., and 0.57 g of 2-[(4-chlorophenyl)(4-piperidinyloxy)methyl]pyridine was added. 0.44 mL of TEA was added dropwise while maintaining the temperature at 0° C., the temperature was gradually raised to room temperature, and the mixture was stirred for 2 hours. DCM phase was concentrated and 10 mL of EtOAC and 10 mL of purified water were added for layer separation. The aqueous layer was further extracted with 10 mL of EtOAc, the residual aqueous layer was discarded, and the organic layer was concentrated. 5 mL of MeOH, 5 mL of purified water and 2.9 mL of TEA were added to the concentrate, and the mixture was refluxed for 4 hours. The MeOH phase was concentrated, 10 mL of EtOAc and 10 mL of purified water were added, and the layers were separated. The organic layer was concentrated under reduced pressure and purified by flash column chromatography to obtain 0.72 g of the title compound as a foam.

Yield: 78.1%

$^1$H NMR (400 MHz, DMSO-d$_6$) δ 9.25 (brs, 2H), 8.47 (d, J=4.8 Hz, 1H), 7.81 (td, J=1.6 and 7.6 Hz, 1H), 7.57 (d, J=8.0 Hz, 1H), 7.44~7.24 (m, 5H), 6.80~6.67 (m, 3H), 5.70 (s, 1H), 3.76 (brs, 1H), 3.66 (brs, 2H), 3.19 (brs, 2H), 1.85 (brs, 2H), 1.53 (brs, 2H)

Example 7: (S)-(4-((4-Chlorophenyl)(pyridin-2-yl) methoxy)piperidin-1-yl)(3,4-dihydroxyphenyl) methanone 0.5 g of 3,4-diacetoxybenzoic acid obtained in Preparation Example 1 was added to DCM 10 mL, and the mixture was stirred at 10° C. 0.66 g of PCl$_5$ was added at 10° C. or lower, the mixture was stirred for 2 hours while maintaining the temperature at 0 to 10° C., and 10 ml of purified water was added for layer separation. The aqueous layer was discarded and the organic layer was dried over Na$_2$SO$_4$ and filtered. The filtrate was concentrated, 10 mL of DCM was added, cooled to 0° C., and 0.57 g of (s)-2-[(4-chlorophenyl) (4-piperidinyloxy)methyl]pyridine was added. 0.44 mL of TEA was added dropwise while maintaining the temperature at 0° C., the temperature was gradually raised to room temperature; and the mixture was stirred for 2 hours. DCM phase was concentrated and 10 mL of EtOAC and 10 mL of purified water were added for layer separation. The aqueous layer was further extracted with 10 mL of EtOAc, the residual aqueous layer was discarded, and the organic layer was concentrated. 5 mL of MeOH, 5 mL of purified water and 2.9 mL of TEA were added to the concentrate, and the mixture was refluxed for 4 hours. The MeOH phase was concentrated, 10 mL of EtOAc and 10 mL of purified water were added, and the layers were separated. The organic layer was concentrated under reduced pressure and purified by flash column chromatography to obtain 0.47 g of the title compound as a foam.

Yield: 51.0%

$^1$H NMR (400 MHz, CDCl$_3$) δ 8.50 (brs, 2H), 7.72 (t, J=6.8 Hz, 1H), 7.52 (d, J=7.6 Hz, 1H), 7.38~7.21 (m, 5H), 6.84 (s, 1H), 6.72 (s, 2H), 5.65 (s, 1H), 3.91 (brs, 1H), 3.69 (brs, 2H), 3.40 (brs, 1H), 3.31 (brs, 1H), 1.73 (brs, 4H)

Example 8: (S)-Methyl-2-(3,4-dihydroxybenzamido)-3-(1H-indol-3-yl)propanoate

To 10 mL of DMF were added 0.5 g (3.24 mmol) of protocatechuic acid, 0.68 g (3.57 mmol) of EDC, 0.48 g (3.57 mmol) of HOBt and 1.58 mL (11.35 mmol) of TEA and 1.0 g (3.89 mmol) of D-tryptophan methylester hydrochloride, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over Na$_2$SO$_4$ and filtered. The filtrate was concentrated with distillation under reduced pressure and purified by flash column chromatography to obtain 0.37 g of the title compound as a foam.

Yield: 33.6%

$^1$H NMR (400 MHz, DMSO-d$_6$) δ 10.84 (s, 1H), 9.51 (s, 1H), 9.14 (s, 1H), 8.42 (d, J=7.2 Hz, 1H), 7.54 (d, J=7.6 Hz, 1H), 7.33 (d, J=8.0 Hz, 1H), 7.26 (d, J=2.0 Hz, 1H), 7.21~7.19 (m, 2H), 7.08~6.97 (m, 2H), 6.75 (d, J=8.0 Hz, 1H), 4.63 (td, J=5.6 and 7.6 Hz, 1H), 3.61 (s, 3H), 3.27~3.21 (m, 2H)

Example 9: 4-(3,4-Dihydroxybenzamido)-1-methyl-3-propyl-1H-pyrazole-5-carboxamide 0.5 g of 3,4-diacetoxybenzoic acid obtained in Preparation Example 1 was added to DCM 10 mL, and the mixture was stirred at 10° C. 0.66 g of PCl$_5$ was added at 10° C. or lower, the mixture was stirred for 2 hours while maintaining the temperature at 0 to 10° C., and 10 ml of purified water was added for layer separation. The aqueous layer was discarded and the organic layer was dried over Na$_2$SO$_4$ and filtered. The filtrate was concentrated, added with 10 mL of DCM, cooled to 0° C., and 0.41 g of 4-amino-1-methyl-3-propyl-1H-pyrazole-5-carboxamide hydrochloride was added. 0.44 mL of TEA was added dropwise while maintaining the temperature at 0° C., the temperature was gradually raised to room temperature, and the mixture was stirred for 2 hours. DCM phase was concentrated and 10 mL of EtOAC and 10 mL of purified water were added for layer separation. The aqueous layer was further extracted with 10 mL of EtOAc, the aqueous layer was discarded, and the organic layer was concentrated. 5 mL of MeOH, 5 mL of purified water and 2.9 mL of TEA were added to the concentrate, and the mixture was refluxed for 4 hours. The MeOH phase was concentrated, 10 mL of EtOAc and 10 mL of purified water were added, and the layers were separated. The organic layer was concentrated by distillation under reduced pressure to give a residue in the form of foam. The residue was crystallized in a mixed solvent of EtOAC/DCM to obtain 0.21 g of the title compound as an off-white solid.

Yield: 31.4%

$^1$H NMR (400 MHz, CDCl$_3$) δ 9.83 (s, 1H), 9.69 (brs, 1H), 9.29 (brs, 1H), 7.38 (d, J=2.0 Hz, 1H), 7.34 (dd, J=2.0 and 8.0 Hz, 1H), 6.84 (d, J=8.4 Hz, 1H), 3.94 (s, 3H), 1.56 (sextet, J=7.2 Hz, 2H), 1.17 (t, J=7.2 Hz, 2H), 0.85 (t, J=7.2 Hz, 3H)

Example 10: 2-Methyl-4-oxo-4H-pyran-3-yl 3,4-dihydroxybenzoate 0.5 g of 3,4-diacetoxybenzoic acid obtained in Preparation Example 1 was added to DCM 10 mL, and the mixture was stirred at 10° C. 0.66 g of PCl$_5$ was added at 10° C. or lower, the mixture was stirred for 2 hours while maintaining the temperature at 0 to 10° C., and 10 ml of purified water was added for layer separation. The aqueous layer was discarded and the organic layer was dried over Na$_2$SO$_4$, and filtered. The filtrate was concentrated, added with 10 mL of DCM, cooled to 0° C., and 0.24 g of maltol was added. 0.44 mL of TEA was added dropwise while maintaining the temperature at 0° C., the temperature was gradually raised to room temperature, and the mixture was stirred for 2 hours, DCM phase was concentrated and 10 mL of EtOAC and 10 mL of purified water were added for layer separation. The aqueous layer was further extracted with 10 mL of EtOAc, the aqueous layer was discarded, and the organic layer was concentrated. 5 mL of MeOH, 5 mL of purified water and 2.9 mL of TEA were added to the concentrate, and the mixture was refluxed for 4 hours. The MeOH phase was concentrated, 10 mL of EtOAc and 10 mL of purified water were added, and the layers were separated. The organic layer was concentrated and sonicated for 5 minutes after addition of a small amount of DCM. The resulting solid was filtered and washed with a small amount of DCM to obtain 0.40 g of the title compound as a white solid.

Yield: 72.6%

$^1$H NMR (400 MHz, CDCl$_3$) δ 9.79 (brs, 2H), 8.19 (d, J=5.6 Hz, 1H), 7.47~7.44 (m, 2H), 6.89 (d, J=8.8 Hz, 1H), 6.46 (d, J=6.0 Hz, 1H), 2.26 (s, 3H)

Example 11: (3,4-Dihydroxyphenyl)(4-phenylpiperazin-1-yl)methanone 0.5 g of 3,4-diacetoxybenzoic acid obtained in Preparation Example 1 was added to DCM 10 mL, and the mixture was stirred at 10° C. 0.66 g of PCl$_5$ was added at 10° C. or lower, the mixture was stirred for 2 hours while maintaining the temperature at 0 to 10° C., and 10 ml of purified water was added for layer separation. The aqueous layer was discarded and the organic layer was dried over Na$_2$SO$_4$ and filtered. The filtrate was concentrated, added with 10 mL of DCM, cooled to 0° C., and 0.31 g of 1-phenylpiperazine was added. 0.44 mL of TEA was added dropwise while maintaining the temperature at 0° C., the temperature was gradually raised to room temperature, and the mixture was stirred for 2 hours. DCM phase was concentrated and 10 mL of EtOAC and 10 mL of purified water were added, followed by layer separation. The aqueous layer was further extracted with 10 mL of EtOAc, the aqueous layer was discarded, and the organic layer was concentrated. 5 mL of MeOH, 5 mL of purified water and 2.9 mL of TEA were added to the concentrate, and the mixture was refluxed for 4 hours. The MeOH phase was concentrated, 10 mL of EtOAc and 10 mL of purified water were added, and the layers were separated. The organic layer was concentrated by distillation under reduced pressure and purified by flash column chromatography to obtain 0.28 g of the title compound as a white solid.

Yield: 45.2%

$^1$H NMR (400 MHz, CDCl$_3$) δ 9.35 (s, 1H), 9.21 (s, 1H), 7.24~7.21 (m, 2H), 6.96~6.75 (m, 6H), 3.62 (brs, 4H), 3.14 (brs, 4H)

Example 12: (6,7-Dihydrothieno[3,2-c]pyridin-5 (4H)-yl)(4-hydroxy-3-methoxyphenyl)methanone 0.5 g of 4-acetoxy-3-methoxybenzoic acid obtained in Preparation Example 2 was added to DCM 10 mL, and the mixture was stirred at 10° C. 0.74 g of PCl$_5$ was added at 10° C. or lower, the mixture was stirred for 2 hours while maintaining the temperature at 0 to 10° C., and 10 ml of purified water was added for layer separation. The aqueous layer was discarded and the organic layer was dried over Na$_2$SO$_4$ and filtered. The filtrate was concentrated, added with 10 mL of DCM, cooled to 0° C., and 0.4 g of 4,5,6,7-tetrahydrothieno[3,2,c]pyridine hydrochloride was added. 0.5 mL of TEA was added dropwise while maintaining the temperature at 0° C., the temperature was gradually raised to room temperature, and the mixture was stirred for 2 hours. DCM phase was concentrated and 10 mL of EtOAC and 10 mL of purified water were added for layer separation. The aqueous layer was further extracted with 10 mL of EtOAc, the aqueous layer was discarded, and the organic layer was concentrated. 5 mL of MeOH, 5 mL of purified water and 3.3 mL of TEA were added to the concentrate, and the mixture was refluxed for 4 hours. The MeOH phase was concentrated, and the resulting solid was filtered and washed with purified water to obtain 0.55 g of the title compound as a white solid.

Yield: 79.9%

$^1$H NMR (400 MHz, DMSO-d$_6$) δ 9.48 (s, 1H), 7.35 (d, J=4.4 Hz, 1H), 7.01 (d, J=1.6 Hz, 1H), 6.93~6.90 (m, 2H), 6.83 (d, J=8.0 Hz, 1H), 4.60 (s, 1H), 3.79 (s, 3H), 3.74 (brs, 2H), 288 (t, J=4.8 Hz, 2H)

Example 13: 2-Ethyl-4-oxo-4H-pyran-3-yl 4-hydroxy-3-methoxybenzoate 0.5 g of 4-acetoxy-3-methoxybenzoic acid obtained in Preparation Example 2 was added to DCM 10 mL, and the mixture was stirred at 10° C. 0.74 g of PCl$_5$ was added at 10° C. or lower, the mixture was stirred for 2 hours while maintaining the temperature at 0 to 10° C., and 10 ml of purified water was added thereto, followed by layer separation. The aqueous layer was discarded and the organic layer was dried over Na$_2$SO$_4$ and filtered. The filtrate was concentrated, 10 mL of DCM was added, cooled to 0° C., and 0.31 g of ethylmaltol was added. 0.5 mL of TEA was added dropwise while maintaining the temperature at 0° C., the temperature was gradually raised to room temperature, and the mixture was stirred for 2 hours. DCM was concentrated and 10 mL of EtOAC and 10 mL of purified water were added, followed by layer separation. The aqueous layer was extracted with 10 mL of EtOAc, the aqueous layer was discarded, and the organic layer was concentrated. 5 mL of MeOH, 5 mL of purified water and 3.3 mL of TEA were added to the concentrate, and the mixture was refluxed for 4 hours. The MeOH was concentrated, 10 mL of EtOAc and 10 mL of purified water were added, and the layers were separated. The organic layer was distilled under reduced pressure and purified by flash column chromatography to obtain 0.34 g of the title compound as a white solid.

Yield: 49.2%

$^1$H NMR (400 MHz, DMSO-d$_6$) δ 10.24 (s, 1H), 8.23 (d, J=5.2 Hz, 1H), 7.63 (d, J=7.6 Hz, 1H), 7.53 (s, 1H), 6.95 (d, J=8.0 Hz, 1H), 6.48 (d, J=5.6 Hz, 1H), 3.85 (s, 3H), 2.62 (q, J=6.8 Hz, 2H), 1.15 (t, J=7.2 Hz, 3H)

Example 14: 2-Methyl-4-oxo-4H-pyran-3-yl 4-hydroxy-3-methoxybenzoate 0.5 g of 4-acetoxy-3-methoxybenzoic acid obtained in Preparation Example 2 was added to DCM 10 mL, and the mixture was stirred at 10° C. 0.74 g of PCl$_5$ was added at 10° C. or lower, the mixture was stirred for 2 hours while maintaining the temperature at 0 to 10° C., and 10 ml of purified water was added thereto, followed by layer separation. The aqueous layer was discarded and the organic layer was dried over Na$_2$SO$_4$ and filtered. The filtrate was concentrated, 10 mL of DCM was added, cooled to 0° C., and 0.27 g of maltol was added. 0.5 mL of TEA was added dropwise while maintaining the temperature at 0° C. the temperature was gradually raised to room temperature, and the mixture was stirred for 2 hours. DCM was concentrated and 10 mL of EtOAC and 10 mL of purified water were added, followed by layer separation. The aqueous layer was extracted with 10 mL of EtOAc, the aqueous layer was discarded, and the organic layer was concentrated. 5 mL of MeOH, 5 mL of purified water and 3.3 mL of TEA were added to the concentrate, and the mixture was refluxed for 4 hours. The MeOH was concentrated, and the resulting solid was filtered and washed with purified water to obtain 0.35 g of the title compound as a white solid.

Yield: 53.2%

$^1$H NMR (400 MHz, DMSO-$d_6$) δ 10.24 (s, 1H), 8.21 (d, J=5.6 Hz, 1H), 7.63 (d, J=8.4 Hz, 1H), 7.53 (s, 1H), 6.95 (d, J=8.0 Hz, 1H), 6.48 (d, J=5.6 Hz, 1H), 3.85 (s, 3H), 2.83 (s, 3H)

Example 15: 4-Hydroxy-3-methoxy-N-(4-methoxy-2-nitrophenyl)benzamide 0.5 g of 4-acetoxy-3-methoxybenzoic acid obtained in Preparation Example 2 was added to DCM 10 mL, and the mixture was stirred at 10° C. 0.74 g of PCl$_5$ was added at 10° C. or lower, the mixture was stirred for 2 hours while maintaining the temperature at 0 to 10° C., and 10 ml of purified water was added thereto, followed by layer separation. The aqueous layer was discarded and the organic layer was dried over Na$_2$SO$_4$ and filtered. The filtrate was concentrated, 10 mL of DCM was added, cooled to 0° C., and 0.40 g of 4-methoxy-2-nitroaniline was added. 0.5 mL of TEA was added dropwise while maintaining the temperature at 0° C., the temperature was gradually raised to room temperature, and the mixture was stirred for 2 hours. DCM was concentrated and 10 mL of EtOAC and 10 mL of purified water were added, followed by layer separation. The aqueous layer was extracted with 10 mL of EtOAc, the aqueous layer was discarded, and the organic layer was concentrated. 5 mL of MeOH, 5 mL of purified water and 3.3 mL of TEA were added to the concentrate, and the mixture was refluxed for 4 hours. The MeOH was concentrated, 10 mL of EtOAc and 10 mL of purified water were added, and the layers were separated. The organic layer was distilled under reduced pressure and purified by flash column chromatography to obtain 0.54 g of the title compound as a red solid.

Yield: 71.3%

$^1$H NMR (400 MHz, DMSO-$d_6$) 10.32 (s, 1H), 9.81 (brs, 1H) 7.63 (d, J=8.8, 1H), 7.52~7.46 (m, 3H), 7.35 (dd, J=2.8 and 8.8, 1H), 3.86 (s, 1H), 3.85 (s, 3H)

Example 16: N-(3-Ethynylphenyl)-4-hydroxy-3-methoxybenzamide 0.5 g of 4-acetoxy-3-methoxybenzoic acid obtained in Preparation Example 2 was added to DCM 10 mL, and the mixture was stirred at 10° C. 0.74 g of PCl$_5$ was added at 10° C. or lower, the mixture was stirred for 2 hours while maintaining the temperature at 0 to 10° C., and 10 ml of purified water was added thereto, followed by layer separation. The aqueous layer was discarded and the organic layer was dried over Na$_2$SO$_4$ and filtered. The filtrate was concentrated, 10 mL of DCM was added, cooled to 0° C., and 0.25 g of 3-aminophenylacetylene was added. 0.5 mL of TEA was added dropwise while maintaining the temperature at 0° C., the temperature was gradually raised to room temperature, and the mixture was stirred for 2 hours, DCM was concentrated and 10 mL of EtOAC and 10 mL of purified water were added, followed by layer separation. The aqueous layer was extracted with 10 mL of EtOAc, the aqueous layer was discarded, and the organic layer was concentrated. 5 mL of MeOH, 5 mL of purified water and 3.3 mL of TEA were added to the concentrate, and the mixture was refluxed for 4 hours. The MeOH was concentrated, 10 mL of EtOAc and 10 mL of purified water were added, and the layers were separated. The organic layer was distilled under reduced pressure. To the resulting solid was added a small amount of IPA and stirred to obtain 0.30 g of the title compound as a white solid.

Yield: 47.2%

$^1$H NMR (400 MHz, DMSO-$d_6$) δ 10.07 (s, 1H), 9.75 (brs, 1H), 7.92 (d, J=1.2 Hz, 1H), 7.80 (dd, J=1.2 and 8.4 Hz, 1H), 7.54~7.50 (m, 2H), 7.36 (t, J=8.0 Hz, 1H), 7.10 (dd, J=1.2 and 8.0 Hz, 1H), 6.90 (d, J=8.0 Hz, 1H), 4.18 (s, 1H), 3.87 (s, 3H)

Example 17: 4-(4-(4-Hydroxy-3-methoxybenzamido)phenoxy)-N-methylpicolinamide 0.5 g of 4-acetoxy-3-methoxybenzoic acid obtained in Preparation Example 2 was added to DCM 10 mL, and the mixture was stirred at 10° C. 0.74 g of PCl$_5$ was added at 10° C. or lower, the mixture was stirred for 2 hours while maintaining the temperature at 0 to 10° C., and 10 ml of purified water was added thereto, followed by layer separation. The aqueous layer was discarded and the organic layer was dried over Na$_2$SO$_4$ and filtered. The filtrate was concentrated, 10 mL of DCM was added, cooled to 0° C., and 0.55 g of 4-(4-aminophenoxy)-N-methylpicolinamide was added. 0.5 mL of TEA was added dropwise while maintaining the temperature at 0° C., the temperature was gradually raised to room temperature, and the mixture was stirred for 2 hours, DCM was concentrated and 10 mL of EtOAC and 10 mL of purified water were added, followed by layer separation. The aqueous layer was extracted with 10 mL of EtOAc, the aqueous layer was discarded, and the organic layer was concentrated. 5 mL of MeOH, 5 mL of purified water and 3.3 mL of TEA were added to the concentrate, and the mixture was refluxed for 4 hours. The MeOH was concentrated. 10 mL of EtOAc and 10 mL of purified water were added, and the layers were separated. The organic layer was distilled under reduced pressure and purified by flash column chromatography to obtain 0.48 g of the title compound as a light yellow solid.

Yield: 51.3%

$^1$H NMR (400 MHz, CDCl$_3$) 8.60 (s, 1H), 8.39 (d, J=5.6, 1H), 8.10 (q, J=5.2, 1H), 7.71~7.65 (m, 3H), 7.52 (d, J=2.0, 1H), 7.43 (dd, J=2.0 and 8.4, 1H), 7.04~6.90 (m, 4H), 6.73 (brs, 1H), 3.78 (s, 3H), 3.01 (d, J=5.2, 3H)

Example 18: 4-((4-Chlorophenyl)(pyridin-2-yl)methoxy)piperidin-1-yl)(4-hydroxy-3-methoxyphenyl)methanone To 10 mL of DMF were added 0.5 g of vanillic acid, 0.51 g of EDC, 0.44 g of HOBt, 1.44 mL of TEA and 0.99 g of 2-[(4-chlorophenyl)(4-piperidinyloxy)methyl]pyridine, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over Na$_2$SO$_4$ and filtered. The filtrate was distilled under reduced pressure and purified by flash column chromatography to obtain 0.40 g of the title compound as a pale yellow solid.

Yield: 31.6%

$^1$H NMR (400 MHz, DMSO-$d_6$) δ 9.41 (brs, 1H), 8.47 (d, J=4.0 Hz, 1H), 7.81 (t, J=7.0, 1H), 7.57 (d, J=8.0 Hz, 1H), 7.44~6.94 (m, 6H), 6.84~6.67 (m, 3H), 5.71 (s, 1H), 3.87 (s, 3H), 3.74~3.69 (m, 2H), 3.37 (brs, 2H), 1.85 (brs, 2H), 1.72 (brs, 2H)

Example 19: 4-Hydroxy-N-((3-hydroxy-5-(hydroxymethylmethyl)-2-methylpyridin-4-yl)methyl)-3-methoxybenzamide To 10 mL of DMF were added 0.5 g of vanillic acid, 0.51 g of EDC, 0.44 g of HOBt, 1.44 mL of TEA and 0.72 g of pyridoxoamine 2HCl, and the mixture was stirred at 60 to 80° C. for 4 hours, 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over $Na_2SO_4$ and filtered. The filtrate was distilled under reduced pressure and purified by flash column chromatography to obtain 0.62 g of the title compound as a pale yellow solid.

Yield: 65.6%

$^1$H NMR (400 MHz, DMSO-$d_6$) 10.50 (s, 1H), 9.76 (s, 1H), 9.18 (t, J=5.6, 1H), 7.29 (s, 1H), 7.47 (d, J=2.0, 1H), 7.42 (dd, J=2.0 and 8.4, 1H), 6.83 (d, J=8.4, 1H), 5.25 (t, J=5.2, 1H), 4.67 (d, J=4.8, 2H), 4.48 (d, J=6.0, 2H), 3.82 (s, 3H), 2.35 (s, 3H)

Example 20: (6,7-Dihydrothieno[3,2-c]pyridin-5(4H)-yl)(2,5-dihydroxyphenyl)methanone To 10 mL of DMF were added 0.5 g of gentisic acid, 0.93 g of EDC, 0.66 g of HOBt, 1.35 mL of TEA and 0.62 g of 4,5,6,7-tetrahydrothieno[3,2,c] pyridine hydrochloride, and the mixture was stirred at 60 to 80° C. for 4 hours. 10 mL of EtOAc and 10 mL of purified water were added to the reaction mixture and stirred. The resulting solid was filtered, refluxed in 10 mL of EtOAc for 1 h and then filtered. The filtrate was washed with a small amount of EtOAc to obtain 0.38 g of the title compound as an apricot-colored solid.

Yield: 42.6%

$^1$H NMR (400 MHz, DMSO-$d_6$) δ 9.08 (s, 1H), 8.93 (s, 1H), 7.34 (brs, 1H), 7.35 (d, J=4.4 Hz, 1H), 7.01 (d, J=1.6 Hz, 1H), 6.93~6.90 (m, 2H), 6.83 (d, J=8.0 Hz, 1H), 4.60 (s, 1H), 3.79 (s, 3H), 3.74 (brs, 2H), 2.86 (t, J=4.8 Hz, 1H)

Example 21: (4-((4-Chlorophenyl)(pyridin-2-yl)methoxy)piperidin-1-yl)(2,5-dihydroxyphenyl)methanone To 10 mL of DMF were added 0.5 g of gentisic acid, 0.68 g of EDC, 0.48 g of HOBt, 1.4 mL of TEA and 1.08 g of 2-[(4-chlorophenyl)(4-piperidinyloxy)methyl]pyridine, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over $Na_2SO_4$ and filtered. The filtrate was distilled under reduced pressure and purified by flash column chromatography to obtain 0.78 g of the title compound as a foam.

Yield: 54.9%

$^1$H NMR (400 MHz, DMSO-$d_6$) 9.05 (s, 1H), 8.89 (s, 1H), 8.47 (dd, J=0.8 and 4.0, 1H), 7.81 (td, J=1.6 and 8.0, 1H), 7.57 (d, J=7.6, 1H), 7.43~7.25 (m, 5H), 6.67~6.60 (m, 2H), 6.46 (d, J=2.8, 1H), 5.69 (s, 1H), 3.93 (brs, 1H), 3.64 (p, J=4.4, 1H), 3.14 (brs, 2H), 1.85 (brs, 1H), 1.55~1.52 (m, 2H)

Example 22: N-((4-(4-Fluorobenzyl)morpholin-2-yl)methyl)-2,5-dihydroxybenzamide To 10 mL of DMF were added 0.5 g of gentisic acid, 0.68 g of EDC, 0.48 g of HOBt, 1.4 mL of TEA and 0.73 g of 3-aminomethyl-4-(4-fluorobenzyl)morpholine, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over $Na_2SO_4$ and filtered. The filtrate was distilled under reduced pressure and purified by flash column chromatography to obtain 0.80 g of the title compound as a foam.

Yield: 68.5%

$^1$H NMR (400 MHz, CDCl$_3$) 7.31~7.27 (m, 2H), 7.05~7.00 (m, 4H), 6.89~6.88 (m, 2H), 3.96~3.67 (m, 4H), 3.49~3.33 (m, 3H), 2.79 (d, J=11.6, 1H), 2.69 (d, J=11.6, 1H), 2.24~1.91 (m, 2H)

Example 23: (2,5-Dihydroxyphenyl)(4-(5-fluorobenzo[d]isoxazol-3-yl)piperidin-1-yl)methanone To 10 mL of DMF were added 0.5 g of gentisic acid, 0.68 g of EDC, 0.48 g of HOBt, 1.4 mL of TEA and 0.83 g of 6-fluoro-3-(4-piperidinyl)-1,2-benzoisoxazole hydrochloride, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer as discarded. The organic layer was washed three times with 10 mL of purified water, dried over $Na_2SO_4$ and filtered. The filtrate was distilled under reduced pressure and purified by flash column chromatography to obtain 0.64 g of the title compound as a white solid.

Yield: 55.4%

$^1$H NMR (400 MHz, DMSO-$d_6$) 9.07 (s, 1H), 8.92 (s, 1H), 8.02 (dd, J=5.6 and 8.8, 1H), 7.70 (dd, J=1.6 and 8.8, 1H), 6.70~6.54 (m, 3H), 4.57 (brs, 1H), 3.61~3.45 (m, 3H), 3.09 (brs, 2H), 2.06 (brs, 2H), 1.80 (brs, 2H)

Example 24: N-(3,4-Dimethoxyphenethyl)-2,5-dihydroxybenzamide

To 10 mL of DMF were added 0.5 g of gentisic acid, 0.68 g of EDC, 0.48 g of HOBt, 1.4 mL of TEA and 0.6 mL of 3,4-dimethoxyphenethylamine, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over $Na_2SO_4$ and filtered. The filtrate was distilled under reduced pressure and purified by flash column chromatography to obtain 0.73 g of the title compound as a white solid.

Yield: 71.0%

$^1$H NMR (400 MHz, DMSO-$d_6$) 11.63 (brs, 1H), 9.00 (brs, 1H), 8.72 (t, J=5.2, 1H), 7.22 (d, J=2.8, 1H), 6.88~6.71 (m, 5H), 3.72 (s, 3H), 3.71 (s, 3H), 3.50 (q, J=6.8, 2H), 2.78 (t, J=7.6, 2H)

Example 25: 2,5-Dihydroxy-N-(2-(thiophen-2-yl)ethyl)benzamide

To 10 mL of DMF were added 0.5 g of gentisic acid, 0.68 g of EDC, 0.48 g of HOBt, 1.4 mL of TEA and 0.4 mL of thiophene-2-ethylamine, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over $Na_2SO_4$ and filtered. The filtrate was distilled under reduced pressure and purified by flash column chromatography to obtain 0.56 g of the title compound as a white solid.

Yield: 65.6%

$^1$H NMR (400 MHz, DMSO-$d_6$) 11.62 (brs, 1H), 9.03 (brs, 1H), 8.83 (t, J=5.2, 1H), 7.34 (dd, J=1.2 and 4.8, 1H), 7.23 (d, J=3.2, 1H), 6.97~6.85 (m, 3H), 6.73 (d, J=8.8, 1H), 3.53 (q, J=6.8, 2H), 3.08 (t, J=6.8, 2H)

Example 26: 2,5-Dihydroxy-N-(2-oxotetrahydrothiophen-3-yl)benzamide

To 10 mL of DMF were added 0.5 g of gentisic acid, 0.68 g of EDC, 0.48 g of HOBt, 1.4 mL of TEA and 0.55 g of homosystein thiolactone hydrochloride, and the mixture was stirred at 60 to 80° C. for 4 hours. 10 mL of EtOAc and 10 mL of purified water were added to the reaction mixture and the layers were separated. The aqueous layer was extracted once with 10 mL of EtOAc and the aqueous layer was discarded. The organic layer was washed three times with 10 mL of purified water, dried over $Na_2SO_4$ and filtered. The filtrate was distilled under reduced pressure and purified by flash column chromatography to obtain 0.21 g of the title compound as a white solid.

Yield: 25.6%

$^1$H NMR (400 MHz, DMSO-$d_6$) 11.33 (brs, 1H), 9.06 (brs, 1H), 8.92 (d, J=8.0, 1H), 7.24 (d, J=3.2, 1H), 6.89 (dd, J=2.8 and 8.8, 1H), 6.77 (d, J=8.8, 1H), 4.84 (sex, J=5.6, 1H), 3.50~3.25 (m, 2H), 2.56~2.26 (m, 2H)

TABLE 1

| Example | Compound | Inhibitory effect of shear stress-induced platelet aggregation |
|---|---|---|
| 1 | | 20~30% |
| 2 | | 20~30% |
| 3 | | 30% or more |
| 4 | | 30% or more |
| 5 | | 20~30% |

TABLE 1-continued
| Example | Compound | Inhibitory effect of shear stress-induced platelet aggregation |
|---|---|---|
| 6 | 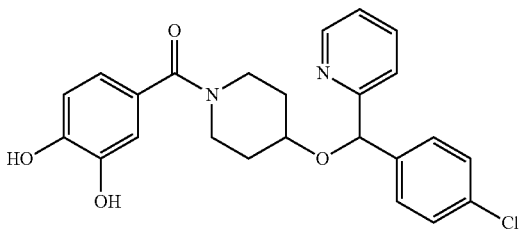 [SMILES: O=C(c1ccc(O)c(O)c1)N1CCC(OC(c2ccc(Cl)cc2)c2ccccn2)CC1] | 20~30% |
| 7 | 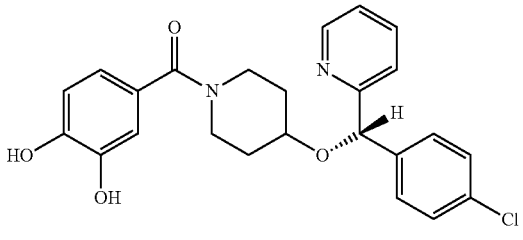 | 20~30% |
| 8 | 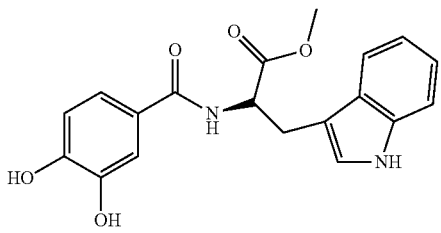 | 20~30% |
| 9 | 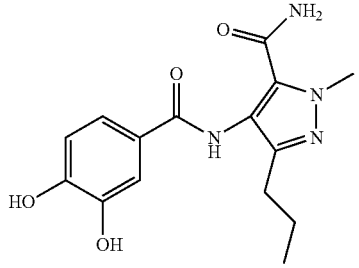 [SMILES: CCCc1nn(C)c(C(N)=O)c1NC(=O)c1ccc(O)c(O)c1] | 20~30% |
| 10 | 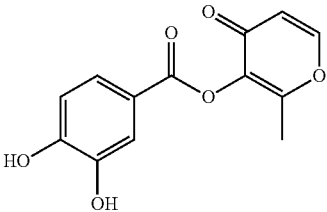 [SMILES: Cc1occc(=O)c1OC(=O)c1ccc(O)c(O)c1] | 20~30% |
| 11 | 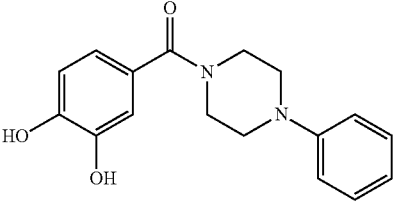 [SMILES: O=C(c1ccc(O)c(O)c1)N1CCN(c2ccccc2)CC1] | 30% or more |

TABLE 1-continued
| Example | Compound | Inhibitory effect of shear stress-induced platelet aggregation |
|---|---|---|
| 12 | 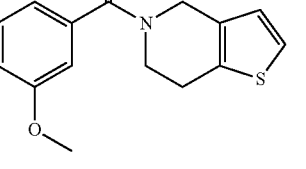 | 20~30% |
| 13 | 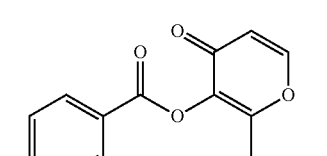 | 20~30% |
| 14 | 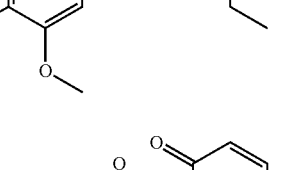 | 30% or more |
| 15 | 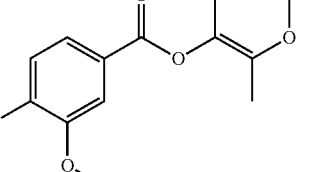 | 20~30% |
| 16 | 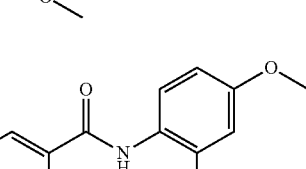 | 30% or more |
| 17 | 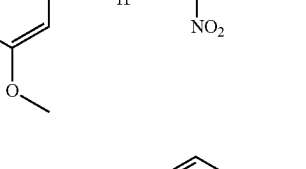 | 20~30% |

TABLE 1-continued

| Example | Compound | Inhibitory effect of shear stress-induced platelet aggregation |
|---------|----------|---------------------------------------------------------------|
| 18 | | 30% or more |
| 19 | | 20~30% |
| 20 | | 30% or more |
| 21 | | 20~30% |
| 22 | | 30% or more |
| 23 | | 20~30% |
| 24 | | 20~30% |

TABLE 1-continued

| Example | Compound | Inhibitory effect of shear stress-induced platelet aggregation |
|---|---|---|
| 25 | [structure: 2,5-dihydroxy-N-(2-(thiophen-2-yl)ethyl)benzamide] | 20~30% |
| 26 | [structure: 2,5-dihydroxy-N-(2-oxotetrahydrothiophen-3-yl)benzamide] | 20~30% |

Experimental Example

Experimental Example 1: Measurement of Inhibitory Effect of Shear Stress-Induced Platelet Aggregation 1-1. Measurement of Platelet Aggregation Inhibitory Effect Using Human Platelet Rich Plasma (PRP)

Blood was collected from the veins of healthy male volunteers who had not taken any medication for more than 2 weeks. All related studies were conducted under the approval of the Seoul National University Institutional Review Board (IRB No. 1305/001-016). During the whole process of study the use of glass containers or glass pipettes was avoided, and the experiments were performed at room temperature. To separate platelet rich plasma (PRP), the blood was collected with 3.2% sodium citrate as an anticoagulant. The whole blood was centrifuged at 150 g for 15 minutes to obtain the supernatant (PRP), and the residue was centrifuged at 2,000 g for 20 minutes to obtain platelet poor plasma (PPP). The number of platelets of the PRP thus obtained was counted with an optical microscope using a hemacytometer. PRP was diluted with PPP so as to include $3 \times 10^8$ platelets per 1 ml, and then used in the experiments. PRP was put on a cone-plate viscometer (RotoVisco 1, Thermo Fischer Scientific, USA), and shear stress was applied to the PRP at 37° C. for 3 minutes at a shear rate of 10,800 s$^{-1}$. In order to evaluate candidate substances, prior to the induction of platelet aggregation, 598.8 μl of PRP was treated with 1.2 μl of 25 μM candidate substance and incubated at 37° C. for 3 minutes using a thermomixer. After applying the shear stress, 20 μl of PRP was fixed in 280 μl of a suspension buffer containing 0.5% glutaraldehyde (134 mM NaCl, 2.9 mM KCl, 1.0 mM MgCl$_2$.6H$_2$O, 10.0 mM HEPES, 5.0 mM dextrose, 12.0 mM NaHCO$_3$, 0.34 mM Na$_2$HPO$_4$, 0.3% BSA, pH 7.4). Then, the number of single platelets in the suspension was counted using a hemacytometer. The degree of inhibition by the candidate substance was calculated according to the following formula (1). The degree of inhibition was determined by the method described below. No shear stress-applied group served as a control, and only shear stress-applied group served as positive control.

Degree of inhibition (%)=[(1−A/B)×100]/[(1−A/C)× 100]    Formula 1

A: Number of single platelets in the shear stress-applied sample after treatment with candidate substance
B: Number of single platelets in the control group with no shear stress applied
C: Number of single platelets in the positive control group with only shear stress applied

TABLE 2

Platelet aggregation inhibitory effect of candidate substances in PRP

| Example | Degree of inhibition (%, Mean ± SEM) |
|---|---|
| 1 | 23 ± 2 |
| 12 | 25 ± 6 |
| 13 | 26 ± 6 |
| 14 | 34 ± 5 |
| 15 | 24 ± 8 |
| 20 | 30 ± 5 |
| 23 | 28 ± 3 |

As shown in Table 2 above, it was confirmed that the effect of inhibiting shear stress-induced platelet aggregation was 30% or more in Example 14 and Example 20 (each 25 μM). In addition, it was confirmed that the inhibitory effect was 20 to 30% in Example 1, Example 12, Example 13, Example 15, and Example 23 (each 25 μM).

1-2. Measurement of Platelet Aggregation Inhibitory Effect Using Human Washed Platelets (WP)

To separate human washed platelets (WP), blood was collected from the veins of healthy males using acid-citrate-dextrose (ACD) as an anticoagulant. At the time of blood collection, platelet activation was inhibited by treatment with 1 μM of prostaglandin E$_1$ (PGE$_1$). The collected blood was centrifuged at 150 g for 15 minutes to obtain PRP from the supernatant, which was centrifuged at 500 g for 10 minutes to obtain platelets. The platelets were suspended in and washed with a washing buffer (134 mM NaCl, 2.9 mM KCl, 1.0 mM MgCl$_2$.6H$_2$O, 10.0 mM HEPES, 5.0 mM dextrose, 12.0 mM NaHCO$_3$, 0.34 mM Na$_2$HPO$_4$, 10% ACD, 0.3% bovine serum albumin, 1 μM PGE$_1$, pH 7.4), and then re-centrifuged at 400 g for 10 minutes. The platelets thus obtained were suspended in the suspension buffer. The number of platelets in WP were counted using a hemacytometer. The platelets were diluted with the suspension buffer so as to include $3 \times 10^8$ platelets per 1 ml, and CaCl$_2$ was added to give a final concentration of 2 mM and then used in the experiments. vWF was added to WP to give a final concentration of 10 μg/ml. WP was put on a cone-plate viscometer, and shear stress was applied to the WP at 37° C. for 3 minutes at a shear rate of 10,800 s$^{-1}$. In order to evaluate efficacy of candidate substances, prior to the induction of platelet aggregation, WP was treated with 10, 25, and 50 μM of candidate substances and incubated at 37° C. for 3 minutes using a thermomixer. After applying the shear stress, 20 μl of WP was fixed in 280 μl of the suspension buffer containing 0.5% glutaraldehyde. Then, the number of single platelets in the suspension was counted using a hemacytometer. The degree of inhibition by the candidate substance was calculated according to formula (1). No shear stress-applied group served as control, and only shear stress-applied group served as a positive control.

TABLE 3

Platelet aggregation inhibitory effect of candidate substances in WP

| Example | | Degree of inhibition (%, Mean ± SEM) |
|---|---|---|
| 1 | 10 μM | 4 ± 3.5 |
|  | 25 μM | 23 ± 1.2 |
|  | 50 μM | 27 ± 1.7 |
| 12 | 10 μM | 10 ± 2.1 |
|  | 25 μM | 30 ± 0.9 |
|  | 50 μM | 33 ± 2.1 |
| 13 | 10 μM | 12 ± 3.8 |
|  | 25 μM | 29 ± 4.1 |
|  | 50 μM | 34 ± 2.7 |
| 14 | 10 μM | 8 ± 1.5 |
|  | 25 μM | 27 ± 2.3 |
|  | 50 μM | 39 ± 0.6 |
| 15 | 10 μM | 14 ± 2.5 |
|  | 25 μM | 26 ± 4.0 |
|  | 50 μM | 36 ± 3.2 |
| 20 | 10 μM | 18 ± 1.5 |
|  | 25 μM | 42 ± 4.2 |
|  | 50 μM | 46 ± 2.1 |

As shown in Table 3 above, it was confirmed that Example 1, Example 12, Example 13, Example 14, Example 15 and Example 20 inhibited shear stress-induced platelet aggregation in WP in a dose-dependent manner.

Experimental Example 2: Evaluation of Drug Efficacy in Arterial Thrombosis Model Vehicle (DMSO: Tween 80: DW=1:2:17) or candidate substance (25 mg/kg) was orally administered to overnight-fasted male Sprague-Dawley rats (250 to 300 g). 30 minutes after administration, the rats were anesthetized by intraperitoneal injection of urethane (1.25 g/kg). The anesthetized animals were restrained on the operating table, and the body temperature was maintained using a heating pad during the entire operating procedure. An incision was made around the neck of the animals to carefully expose the right carotid artery, and the adipose tissues attached to the blood vessels were carefully removed. Doppler flow probe (0.5 mm-diameter, MA0.5PSB, Transonic System Inc., USA) was fixed to the exposed carotid artery, and a doppler flow-meter (TS420, Transonic System Inc., USA) was connected thereto. 60 minutes after oral administration, a piece of Whatman No. 1 filter paper (2 mm×1 mm) soaked with 50% FeCl$_3$ solution was attached to the underlying blood vessels to which the probe was fixed. The filter paper was removed after 10 minutes, and the change of blood flow due to thrombus formation in the carotid artery was measured for 60 minutes after the time point of removal. The occlusion time was defined as the time at which the blood flow became zero more than one minute for the first time.

TABLE 4

Thrombogenesis inhibitory effect of candidate substances

| Example | Time of thrombogenesis (second) | Fold (vs. Control) |
|---|---|---|
| Control | 356 ± 38 | — |
| 1 | 936 ± 120 | 2.6 |
| 12 | 665 ± 77 | 1.9 |
| 13 | 752 ± 69 | 2.1 |
| 14 | 615 ± 54 | 1.7 |
| 15 | 816 ± 78 | 2.3 |
| 20 | 2122 ± 265 | 6.0 |
| 23 | 674 ± 92 | 1.9 |

As shown in Table 4 above, it was confirmed that the candidate substances exhibiting the effect of 2.5 times or more as compared with the control in the iron chloride (FeCl$_3$)-induced thrombogenesis model are Example 1 and Example 20.

Experimental Example 3: Measurement of Thrombosis Inhibitory Effect of Candidate Substances in the Carotid Artery Shear Stress Model Vehicle (0.5% methylcellulose), clopidogrel (8 mg/kg), aspirin (50 mg/kg) or a candidate substance was orally administered to male Sprague-Dawley rats (250 to 300 g). 2 hours after administration, the rats were anesthetized by ketamine/rompun (ketamine/xylazine) cocktail 0.1 ml/100 g. Except for the normal control group, the right cervical skin of the experimental animals was incised to expose the common carotid artery. A surgical tube with a length of 1 mm and an inside diameter of 0.58 mm was inserted into the exposed carotid artery and tied with a single thread. The exposed site and the operation site were treated with an anti-adhesion agent, and then sutured for the animals to recover. After the surgery, vehicle, clopidogrel, aspirin or a candidate substance was orally administered to the rats twice a day for 3 days. On the fourth day, 2 hours after the final administration, urethane (100 mg/300 μl/100 g) was administered intraperitoneally to the rats to induce anesthesia, and the operation site was opened to separate a total of 1 cm of the blood vessel, 5 mm above and 5 mm below the surgical tube. The separated blood vessel was perfused with 0.2 ml of 0.9% saline at 0.3 ml/min to remove the remaining blood, and then maintained in 1 ml of protein lysis buffer (NaOH 2 g, Na$_2$CO$_3$ 0.1 g in 500 ml D.W). After collected, the blood vessel thrombus was double-boiled in boiling water together with the protein lysis buffer. 200 μl of the reaction solution (10 ml bicinchoninic acid solution+200 μl 4% aqueous solution of copper sulfate) was added to 10 μl of the heated thrombus, and the mixture was reacted at 37° C. for 30 minutes and quantified with an ELISA reader (562 nm).

TABLE 5

Thrombosis inhibitory effect of candidate substances in the carotid artery shear stress model

| Substance administered | Dose (mg/kg) | Operation | Amount of thrombus (mg, Mean ± SEM) |
|---|---|---|---|
| Normal C. | — | x | 0.005 ± 0.002 |
| Negative C. | — | o | 0.124 ± 0.007 |
| Clopidogrel | 8 | o | 0.067 ± 0.004 |
| Aspirin | 50 | o | 0.092 ± 0.007 |
| Example 1 | 25 | o | 0.065 ± 0.005 |
| Example 12 | 25 | o | 0.069 ± 0.007 |
| Example 13 | 25 | o | 0.064 ± 0.006 |

TABLE 5-continued

Thrombosis inhibitory effect of candidate substances
in the carotid artery shear stress model

| Substance administered | Dose (mg/kg) | Operation | Amount of thrombus (mg, Mean ± SEM) |
|---|---|---|---|
| Example 14 | 25 | ○ | 0.066 ± 0.006 |
| Example 15 | 25 | ○ | 0.070 ± 0.006 |
| Example 20 | 25 | ○ | 0.068 ± 0.005 |
| Example 23 | 25 | ○ | 0.071 ± 0.006 |

As shown in Table 5 above, it was confirmed that in the animals each orally administered with Example 1, Example 12, Example 13, Example 14, Example 15, Example 20, and Example 23, the shear stress-induced thrombogenesis was significantly, remarkably inhibited compared with the control group. This suggested that the degree of inhibition of the candidate substances against the thrombogenesis is as good as comparable to that of clopidogrel when compared with the group administered with clopidogrel, which is the most commonly used antiplatelet agent.

Degree of inhibition (%)=100−[(C−A)×100/(B−A)]    Formula 2

A: Amount of thrombus in Normal Control
B: Amount of thrombus in Negative Control
C: Amount of thrombus in candidate substance treatment Experimental Example 4: Measurement of Inhibitory Effect of Candidate Substances for Chemical Agonist (Physiological Agonist)-Induced Platelet Aggregation To investigate whether the candidate substance has inhibition selectivity for shear-stress-induced platelet aggregation, which is by a physical stimulus, the inhibitory effect of the candidate substance was investigated in is experiment was conducted by activating platelets with physiological agonists—i.e., thrombin, collagen and ADP—to study the inhibitory effect of the candidate substance.

Human PRP (598.8 μl) was treated with 1.2 μl of the candidate substance per concentration (25, 100, 250 μM) and reacted at 37° C. for 3 minutes using a thermomixer. Then, PRP (495 μl) was put in the aggregometer cuvette and preincubated for 1 minute, followed by treatment with platelet aggregation-inducing reagent, thrombin (0.6-0.8 U/ml), collagen (2-5 μg/ml), or ADP (adenosine diphosphate, 15-20 μM) at the minimum concentration causing maximum aggregation. The degree of aggregation of the platelets was measured by a turbidity change using a lumi-aggregometer (Chrono-Log Co., USA). The turbidity of the PRP was considered as 0%, and the turbidity of the PPP was considered as 100%. During the measurement, the reaction mixture was continuously stirred at 1,000 rpm with a silicone-coated magnetic stir bar. The reaction was observed for 5 minutes for thrombin or ADP, and 6 minutes for collagen.

TABLE 6

Results of measurement of the degree of aggregation by thrombin

| Example | | Degree of platelet aggregation (%, Mean ± SEM) |
|---|---|---|
| Thrombin | | 83.5 ± 6.5 |
| 1 | 25 μM | 88.0 ± 2.1 |
|  | 100 μM | 88.7 ± 6.1 |
|  | 250 μM | 78.7 ± 1.8 |
| 12 | 25 μM | 99.5 ± 7.5 |
|  | 100 μM | 95.0 ± 12.0 |
|  | 250 μM | 88.5 ± 4.5 |
| 13 | 25 μM | 92.5 ± 5.5 |
|  | 100 μM | 95.0 ± 12.0 |
|  | 250 μM | 88.5 ± 4.5 |
| 14 | 25 μM | 81.3 ± 2.5 |
|  | 100 μM | 84.0 ± 0.6 |
|  | 250 μM | 86.0 ± 4.6 |
| 15 | 25 μM | 95.5 ± 3.5 |
|  | 100 μM | 100.5 ± 4.5 |
|  | 250 μM | 98.0 ± 3.0 |
| 20 | 25 μM | 84.0 ± 3.2 |
|  | 100 μM | 82.3 ± 3.7 |
|  | 250 μM | 82.0 ± 15.0 |
| 23 | 25 μM | 96.0 ± 4.0 |
|  | 100 μM | 88.5 ± 6.5 |
|  | 250 μM | 93.5 ± 1.5 |
| DTI[1] | 2 μM | 11.5 ± 1.2 |

[1]DTI: Direct Thrombin Inhibitor

As shown in Table 6 above, it was confirmed that when compared with the group treated with thrombin only, the candidate substances did not show the platelet aggregation inhibitory effect up to 250 μM. In contrast, it was confirmed that the platelet aggregation was inhibited when the positive control DTI was treated.

TABLE 7

Results of measurement of the degree of aggregation by collagen

| Example | | Degree of platelet aggregation (%, Mean ± SEM) |
|---|---|---|
| Collagen | | 82.6 ± 1.2 |
| 1 | 25 μM | 84.3 ± 3.5 |
|  | 100 μM | 80.7 ± 10.2 |
|  | 250 μM | 84.3 ± 3.8 |
| 12 | 25 μM | 83.0 ± 4.0 |
|  | 100 μM | 80.0 ± 2.0 |
|  | 250 μM | 87.5 ± 3.5 |
| 13 | 25 μM | 90.0 ± 3.0 |
|  | 100 μM | 79.5 ± 0.5 |
|  | 250 μM | 85.5 ± 3.5 |
| 14 | 25 μM | 82.0 ± 1.7 |
|  | 100 μM | 80.0 ± 1.7 |
|  | 250 μM | 92.0 ± 2.0 |
| 15 | 25 μM | 86.0 ± 0.0 |
|  | 100 μM | 84.5 ± 4.5 |
|  | 250 μM | 83.5 ± 3.5 |
| 20 | 25 μM | 82.3 ± 5.8 |
|  | 100 μM | 81.3 ± 3.5 |
|  | 250 μM | 87.7 ± 2.0 |
| 23 | 25 μM | 82.0 ± 5.0 |
|  | 100 μM | 84.5 ± 4.5 |
|  | 250 μM | 83.5 ± 2.5 |

As shown in Table 7 above, it was confirmed that when compared with the group treated with collagen only, the candidate substances did not show the platelet aggregation inhibitory effect up to 250 μM.

TABLE 8

Results of measurement of the degree of aggregation by ADP

| Example | | Degree of platelet aggregation (%, Mean ± SEM) |
|---|---|---|
| ADP | | 76.0 ± 1.3 |
| 1 | 25 μM | 77.5 ± 3.5 |
| | 100 μM | 69.0 ± 6.0 |
| | 250 μM | 78.0 ± 7.0 |
| 12 | 25 μM | 76.0 ± 3.0 |
| | 100 μM | 67.5 ± 2.5 |
| | 250 μM | 77.0 ± 12.0 |
| 13 | 25 μM | 75.5 ± 1.5 |
| | 100 μM | 75.0 ± 1.0 |
| | 250 μM | 71.5 ± 6.5 |
| 14 | 25 μM | 74.5 ± 2.5 |
| | 100 μM | 75.0 ± 3.0 |
| | 250 μM | 63.5 ± 5.5 |
| 15 | 25 μM | 70.5 ± 2.5 |
| | 100 μM | 68.5 ± 3.5 |
| | 250 μM | 67.0 ± 4.0 |
| 20 | 25 μM | 73.0 ± 2.0 |
| | 100 μM | 69.0 ± 1.0 |
| | 250 μM | 66.5 ± 2.5 |
| 23 | 25 μM | 73.5 ± 1.5 |
| | 100 μM | 66.0 ± 1.0 |
| | 250 μM | 65.0 ± 0.0 |
| Clopidogrel | 40 μM | 18.3 ± 3.4 |

As shown in Table 8 above, it was confirmed that when compared with the group treated with ADP only, the candidate substances did not show the platelet aggregation inhibitory effect up to 250 μM. In contrast, it was confirmed that the platelet aggregation was inhibited when the positive control clopidogrel was treated.

Experimental Example 5: Evaluation of Cytotoxicity of Candidate Substances 5-1. Evaluation of Cytotoxicity of Candidate Substances Using EA.hy926 Cell Line Experiments were conducted to determine the cytotoxicity of candidate substances in human vascular endothelial cells (EA.hy926). EA.hy926 was passaged in DMEM (Dulbecco's Minimum Essential Medium) supplemented with 10% fetal bovine serum (FBS) at 5% $CO_2$/37° C. The cells were cultured in a 96 well plate at $1×10^4$ cells/well for 48 hours, washed twice with DMEM and then cultured for 24 hours. Candidate substances were prepared at final concentrations of 25 and 100 μM, applied to the wells at 200 μl per well and cultured for 24 hours. MTT assay was used to measure the absorbance at 570 nm after colorization in violet.

TABLE 9

Results of evaluation of cytotoxicity of candidate substances in the EA.hy926 cell line

| Example | Concentration (μM) | Cell viability (%) |
|---|---|---|
| 1 | 25 | 92.2 ± 2.8 |
| | 100 | 94.2 ± 1.9 |
| 12 | 25 | 95.1 ± 1.9 |
| | 100 | 97.2 ± 2.8 |
| 13 | 25 | 100.1 ± 1.9 |
| | 100 | 94.2 ± 2.0 |
| 14 | 25 | 99.6 ± 1.7 |
| | 100 | 99.5 ± 1.6 |
| 15 | 25 | 100.8 ± 2.5 |
| | 100 | 94.9 ± 3.3 |
| 20 | 25 | 99.7 ± 3.2 |
| | 100 | 97.7 ± 2.2 |
| 23 | 25 | 104.3 ± 1.8 |
| | 100 | 99.9 ± 1.9 |

As shown in Table 9 above, it was confirmed that the candidate substances did not show toxicity up to 100 μM in the Ea.hy926 cell line.

5-2. Evaluation of Cytotoxicity of Candidate Substances Using Human Platelets

Leakage of lactate dehydrogenase (LDH) from the platelets was measured by a spectro-photometry method. 1.2 μl of the test substance was added to 598.8 μl of PRP, and the mixture was reacted at 37° C. for 3 minutes using a thermomixer. After the reaction, 100 μl of the sample was centrifuged at 12,000 g for 2 minutes, and 80 μl of the supernatant was taken and refrigerated until evaluation. The evaluation was performed within 24 hours. The control group (positive control) was treated with 50 μM digitonin for 1 hour. 25 μl of the sample was added to 1 ml of a pre-warmed Tris-EDTA NADH solution (56 mM Tris(hydroxymethyl) aminomethane, 5.6 mM EDTA, 0.17 mM β-NADH pH 7.4) and reacted for 5 minutes at 37° C. Then, 100 μl of a 14 mM pyruvate solution previously heated at 37° C. was added to the reaction mixture, and absorbance was immediately measured at a wavelength of 339 nm for 1 minute using a spectrophotometer (UV-Vis spectrophotometer, UV-2201, Shidamadzu, Japan). The rate of decrease in absorbance means the rate of oxidation of NADH, indicating the activity of LDH liberated from platelets. Total activity of LDH was measured by inducing lysis of platelets with 0.3% Triton X-100. The basal level of LDH (Control) was measured in plasma. The activity of each sample was measured as a percentage of the total activity of LDH.

TABLE 10

Results of evaluation of cytotoxicity of candidate substances in platelets

| Example | | LDH leakage (%, Mean ± SEM) |
|---|---|---|
| Digitonin | 50 μM | 80.4 ± 1.7 |
| 1 | 25 μM | 2.7 ± 0.5 |
| | 100 μM | 2.4 ± 0.2 |
| | 250 μM | 2.7 ± 0.5 |
| 12 | 25 μM | 2.3 ± 0.5 |
| | 100 μM | 3.6 ± 0.1 |
| | 250 μM | 3.6 ± 0.8 |
| 13 | 25 μM | 2.2 ± 0.4 |
| | 100 μM | 4.0 ± 1.2 |
| | 250 μM | 4.0 ± 0.3 |
| 14 | 25 μM | 4.8 ± 0.2 |
| | 100 μM | 5.6 ± 0.9 |
| | 250 μM | 4.2 ± 0.9 |
| 15 | 25 μM | 2.7 ± 0.1 |
| | 100 μM | 3.2 ± 0.4 |
| | 250 μM | 3.1 ± 1.3 |
| 20 | 25 μM | 4.1 ± 0.7 |
| | 100 μM | 5.2 ± 0.4 |
| | 250 μM | 3.5 ± 1.2 |
| 23 | 25 μM | 1.8 ± 0.1 |
| | 100 μM | 2.2 ± 1.3 |
| | 250 μM | 3.2 ± 0.5 |

As shown in Table 10 above, it was confirmed that the candidate substances did not show toxicity up to 250 μM in the platelets.

5-3. Evaluation of Cytotoxicity of Candidate Substances Using Human Liver Cells

Experiments were conducted to evaluate cytotoxicity in human liver cells (HepG2). HepG2 cells, which are human liver carcinoma cell lines, were cultured in DMEM (Dulbecco's minimum essential medium) supplemented with 10% FBS (fetal bovine serum) and 1% Penicillin/Streptomycin at 37° C. and 5% $CO_2$. The cells were cultured in a 48 well plate at $4 \times 10^4$ cells/well for 24 hours and then used in the experiments. The HepG2 cells were treated with the candidate substances (250 μM) for 18 hours, and then the medium was removed and WST-1 was added, followed by shading for 3 hours for reaction. After 3 hours, the supernatant was taken and absorbance was measured at 450 nm. Cell viability was calculated by comparing the absorbance measured after adding WST-1 to HepG2 cells not treated with the candidate substances. Acetaminophen (40 mM) was used as a control.

TABLE 11

Results of evaluation of cytotoxicity of 250 μM of candidate substances in HepG2 cell line

| Example | Cell vaibility (%) |
|---|---|
| Acetaminophen | 35.3 ± 3.5 |
| 1 | 91.7 ± 2.0 |
| 12 | 89.0 ± 2.3 |
| 13 | 98.3 ± 5.5 |
| 14 | 87.3 ± 2.7 |
| 15 | 89.7 ± 2.3 |
| 20 | 87.7 ± 2.6 |
| 23 | 82.7 ± 5.5 |

As shown in Table 11 above, it was confirmed that the candidate substances did not show hepatotoxicity up to 250 μM in the HepG2 cell line.

Experimental Example 6: Measurement of Plasma Coagulation Time

In order to separate plasma, blood was collected with 3.2% sodium citrate as an anticoagulant. Whole blood was centrifuged at 2000 g for 20 minutes to obtain plasma. After treating the plasma with the test substances for 3 minutes, plasma coagulation time was measured. For plasma coagulation time, Activated Partial Thromboplastin Time (aPTT) and Prothrombin Time (PT) were measured using BBL® Fibrometer (Becton Dickinson, Cockeysville, Md.). For measurement of aPTT, the plasma was treated with aPTT reagents in fibrometer cup and reacted at 37° C. for 3 min. After the reaction, $CaCl_2$ was added and blood coagulation time was measured immediately. For the measurement of PT, PT reagent was added to warmed plasma, and blood coagulation time was measured immediately. DTI, known to prolong plasma coagulation time, was used as a control.

TABLE 12

Results of measurement of plasma coagulation time - aPTT

| Example | | Time (sec) |
|---|---|---|
| Control | | 25.5 ± 0.8 |
| 1 | 25 μM | 23.8 ± 1.9 |
| | 100 μM | 24.8 ± 2.0 |
| | 250 μM | 26.7 ± 0.8 |
| 12 | 25 μM | 24.3 ± 0.1 |
| | 100 μM | 26.7 ± 1.0 |
| | 250 μM | 27.2 ± 2.0 |
| 13 | 25 μM | 24.7 ± 1.0 |
| | 100 μM | 26.6 ± 1.8 |
| | 250 μM | 27.5 ± 1.7 |
| 14 | 25 μM | 27.0 ± 0.4 |
| | 100 μM | 26.7 ± 0.2 |
| | 250 μM | 26.3 ± 1.7 |
| 15 | 25 μM | 26.3 ± 2.3 |
| | 100 μM | 26.6 ± 1.0 |
| | 250 μM | 29.3 ± 0.5 |
| 20 | 25 μM | 24.9 ± 1.0 |
| | 100 μM | 25.3 ± 0.6 |
| | 250 μM | 25.8 ± 0.9 |
| 23 | 25 μM | 26.2 ± 0.2 |
| | 100 μM | 29.5 ± 1.2 |
| | 250 μM | 26.1 ± 0.2 |
| DTI | 2 μM | 86.6 ± 2.4 |

As shown in Table 12 above, it was confirmed that the candidate substances did not significantly change the aPTT points compared with Control, which indicates that the candidate substances did not affect aPTT.

TABLE 13

Results of measurement of plasma coagulation time - PT

| Example | | Time (sec) |
|---|---|---|
| Control | | 10.4 ± 0.2 |
| 1 | 25 μM | 10.8 ± 0.5 |
| | 100 μM | 10.7 ± 0.8 |
| | 250 μM | 11.0 ± 0.1 |
| 12 | 25 μM | 10.9 ± 0.1 |
| | 100 μM | 11.0 ± 0.5 |
| | 250 μM | 10.5 ± 0.3 |
| 13 | 25 μM | 11.0 ± 0.3 |
| | 100 μM | 10.6 ± 0.2 |
| | 250 μM | 10.8 ± 0.3 |
| 14 | 25 μM | 10.1 ± 0.3 |
| | 100 μM | 10.1 ± 0.0 |
| | 250 μM | 11.1 ± 0.1 |
| 15 | 25 μM | 10.7 ± 0.0 |
| | 100 μM | 10.6 ± 0.2 |
| | 250 μM | 10.9 ± 0.1 |
| 20 | 25 μM | 10.8 ± 0.4 |
| | 100 μM | 10.2 ± 0.4 |
| | 250 μM | 11.2 ± 0.4 |
| 23 | 25 μM | 10.3 ± 0.1 |
| | 100 μM | 10.7 ± 0.2 |
| | 250 μM | 10.8 ± 0.3 |
| DTI | 2 μM | 47.1 ± 1.8 |

As shown in Table 13 above, it was confirmed that the candidate substances did not significantly change the PT points compared with Control, which indicates that the candidate substances did not affect PT.

Experimental Example 7: Evaluation of Bleeding Side Effect (Bleeding Time) in Experimental Animals Male Sprague-Dawley rats (250 to 300 g) were fasted overnight and then were orally administered with the candidate substances at each concentration. After 1 hour, the rats were anesthetized by intraperitoneal injection of urethane (1.25 g/kg). The 3 mm portion of the tail tip of the rats was cut and carefully wiped every 30 seconds. Bleeding time was measured in hours until no more blood was drawn, and when the bleeding lasted longer than 30 minutes, the bleeding time was recorded as 30 minutes.

TABLE 14

| Example | | Bleeding time (min) |
|---|---|---|
| Control | | 6.2 ± 0.4 |
| 1 | 25 μM | 6.0 ± 0.9 |
| | 100 μM | 6.5 ± 0.9 |
| 12 | 25 μM | 6.3 ± 0.6 |
| | 100 μM | 6.5 ± 0.3 |
| 13 | 25 μM | 6.5 ± 0.6 |
| | 100 μM | 7.2 ± 0.3 |
| 14 | 25 μM | 6.7 ± 0.9 |
| | 100 μM | 6.3 ± 0.6 |
| 15 | 25 μM | 7.3 ± 0.7 |
| | 100 μM | 6.2 ± 0.6 |
| 20 | 25 μM | 6.7 ± 0.6 |
| | 100 μM | 7.7 ± 0.4 |
| Aspirin | 25 μM | 9.5 ± 0.8 |
| | 100 μM | 15.1 ± 0.8 |
| Clopidogrel | 2.5 μM | 14.3 ± 1.6 |
| | 25 μM | 26.8 ± 1.6 |

As shown in Table 14 above, bleeding, which is expected to be a side effect of the candidate substances, was found to be lower than that of clopidogrel and aspirin as control substances. It was confirmed that all of the compounds of the Examples did not show side effects of bleeding.

Experimental Example 8: Evaluation of Bleeding Side Effect by Repeated Administration Candidate substances (50 mg/kg), clopidogrel (15 mg/kg), or aspirin (100 mg/kg) was each orally administered to ICR mouse (male, 35 to 40 g) once daily for 7 days. One hour after the last administration, the mice were anesthetized by breathing, and the 4 mm portion from the tail tip of the mice was cut. Then, the tail tip of the mice was immersed in a transparent 15-ml tube containing the pre-prepared 37° C. saline. The time when blood was not spread any more and the bleeding stopped was measured.

TABLE 15

| Example | Dose (mg/kg) | Bleeding time (min) |
|---|---|---|
| Control | — | 1.6 ± 0.3 |
| Clopidogrel | 15 | 35.4 ± 2.9 |
| Aspirin | 100 | 12.3 ± 0.7 |
| Example 13 | 50 | 1.6 ± 0.4 |
| Example 14 | 50 | 1.6 ± 0.3 |

As shown in Table 15 above, the time taken to stop bleeding at the clinical dose exceeded 35 minutes in the case of clopidogrel, and thus the bleeding time was delayed by about 22 times compared with the control group. In the case of aspirin, the time taken to stop bleeding exceeded 12 minutes, and thus the bleeding time was delayed by about 7.6 times. However, when the compounds of Example 13 and Example 14 were repeatedly administered once a day for 7 days, the time taken to stop bleeding was almost the same as that of the control, and the bleeding time was about 1 minute and 30 seconds. Therefore, almost no bleeding side effect was observed for the candidate substances, and it was confirmed that the candidate substances are a new antiplatelet agent candidate that overcomes the bleeding side effect problem of the existing antiplatelet agents.

Experimental Example 9: 2-Week Repeat-Dose Toxicity Study

After oral administration of vehicle (0.5% methylcellulose) or the candidate substances at low dose, medium dose, and high dose (100, 300, 1000 mg/kg) to ICR mice (female, male, 18 to 26 g) once a day for 2 weeks, the NOAEL values of the candidate substances were calculated by observing and recording mortality, body weight change, clinical observations, food and drinking water consumption, gross necropsy findings, histopathological evaluation of abnormal organ, and organ weights.

TABLE 16

| Example | NOAEL (No observed adverse effect level) |
|---|---|
| Example 13 | >1000 mg/kg |
| Example 14 | >1000 mg/kg |

As shown in Table 16 above, when the compounds of Example 13 or Example 14 were orally administered at doses of 100, 300 and 1000 mg/kg once a day for 2 weeks, no dead animals were observed, and no abnormal findings were observed in body weight change, clinical observations, food and drinking water consumption, gross necropsy findings, and organ weights. Therefore, it was confirmed that the NOAEL value of the candidate substances might be 1000 mg/kg or more.

Experimental Example 10: Statistics

The significance of the test results was assessed as significant when p was 0.05 or less via the Student's t-test and the one-way ANOVA test.

What is claimed is:
1. A compound represented by the following Formula (I) or (II), or a pharmaceutically acceptable salt or stereoisomer thereof:

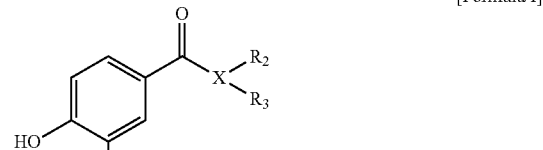

[Formula I]

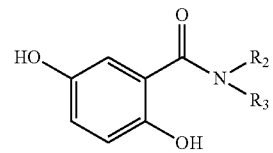

[Formula II]

wherein,
$R_1$ is hydroxy or $C_1$-$C_{10}$ alkoxy;
X is N or O;
$R_2$ is —$(CH_2)_p$-5- to 12-membered heterocycle-$(CH_2)_p$—$C_6$-$C_{12}$ aryl, 5- to 12-membered heterocycle, —$(CH_2)_p$—NHC(=O)—$C_6$-$C_{12}$ aryl, —$CHR_4R_5$, 5- to 12-membered heteroaryl, $C_6$-$C_{12}$ aryl, —$C_6$-$C_{12}$ aryl-O-5- to 12-membered heteroaryl, or —$(CH_2)_p$-5- to 12-membered heteroaryl, provided that when $R_2$ is $(CH_2)_p$-5- to 12-membered heteroaryl, the heteroaryl is not pyrazine, pyridine or indole, and when $R_2$ is 5- to 12-membered heteroaryl, the heteroaryl is not benzothiazole;

wherein p is an integer of 1 to 10; $R_4$ and $R_5$ are each independently $C_1$-$C_6$ alkoxycarbonyl or —$CH_2$-5- to 12-membered heteroaryl;

wherein said heterocycle and heteroaryl may contain 1 to 3 heteroatoms selected from N, O and S; said aryl can be substituted with 1 to 4 substituents selected from the group consisting of aminocarbonyl, nitro, nitrile, $C_1$-$C_6$ alkylaminocarbonyl, and hydroxy-$C_1$-$C_6$ alkyl and said heterocycle and heteroaryl is substituted with 1 to 4 substituents selected from the group consisting of halogen, oxo, aminocarbonyl, nitro, $C_1$-$C_6$ alkoxy, nitrile, $C_1$-$C_6$ alkylamino carbonyl, hydroxyl, and hydroxyl-$C_1$-$C_6$ alkyl;

$R_3$ is hydrogen;

when X is O, $R_3$ does not exist; or when X is N, X taken together with $R_2$ and $R_3$ may form a 5- to 12-membered heterocycle containing 1 to 3 heteroatoms selected from O, N and S; wherein said heterocycle can be substituted with $C_6$-$C_{12}$ aryl; a 6- to 12-membered heteroaryl containing 1 to 3 heteroatoms selected from O, N and S, which is unsubstituted or substituted with halogen; or —O—$CHR_6R_7$; and wherein $R_6$ and $R_7$ are each independently $C_6$-$C_{12}$ aryl or a 6- to 10-membered heteroaryl containing 1 to 3 heteroatoms selected from N, O and S, both of which are unsubstituted or substituted with halogen, provided that when X is N, X taken together with $R_2$ and $R_3$ forms a 6-membered heterocycle, said heterocycle is substituted with $C_6$-$C_{12}$ aryl; a 6- to 12-membered heteroaryl containing 1 to 3 heteroatoms selected from O, N, and S, which is unsubstituted or substituted with halogen or —$OCHR_6R_7$.

2. A compound which is selected from the following group:

(6,7-Dihydrothieno[3,2-c]pyridin-5(4H)-yl)(3,4-dihydroxyphenyl)methanone;

(3,4-Dihydroxyphenyl)(4-(5-fluorobenzo[d]isoxazol-3-yl)piperidin-1-yl)methanone;

N-((4-(4-Fluorobenzyl)morpholin-2-yl)methyl)-3,4-dihydroxybenzamide;

3,4-Dihydroxy-N-(2-oxotetrahydrothiophen-3-yl)benzamide;

N, N'-(Nonan-1,9-diyl)bis(3,4-dihydroxybenzamide);

(4-((4-Chlorophenyl)(pyridin-2-yl)methoxy)piperidin-1-yl)(3,4-dihydroxyphenyl)methanone;

(S)-(4-((4-Chlorophenyl)(pyridin-2-yl)methoxy)piperidin-1-yl)(3,4-dihydroxyphenyl)methanone;

(S)-Methyl-2-(3,4-dihydroxybenzamido)-3-(1H-indol-3-yl)propanoate;

4-(3,4-Dihydroxybenzamido)-1-methyl-3-propyl-1H-pyrazole-5-carboxamide;

2-Methyl-4-oxo-4H-pyran-3-yl 3,4-dihydroxybenzoate;

(3,4-Dihydroxyphenyl)(4-phenylpiperazin-1-yl)methanone;

(6,7-Dihydrothieno[3,2-c]pyridin-5(4H)-yl)(4-hydroxy-3-methoxyphenyl)methanone;

2-Ethyl-4-oxo-4H-pyran-3-yl 4-hydroxy-3-methoxybenzoate;

2-Methyl-4-oxo-4H-pyran-3-yl 4-hydroxy-3-methoxybenzoate;

4-Hydroxy-3-methoxy-N-(4-methoxy-2-nitrophenyl)benzamide;

4-(4-(4-Hydroxy-3-methoxybenzamido)phenoxy)-N-methylpicolinamide;

4-((4-Chlorophenyl)(pyridin-2-yl)methoxy)piperidin-1-yl)(4-hydroxy-3-methoxyphenyl)methanone;

4-Hydroxy-N-((3-hydroxy-5-(hydroxymethyl)-2-methylpyridin-4-yl)methyl)-3-methoxybenzamide;

(6,7-Dihydrothieno[3,2-c]pyridin-5(4H)-yl)(2,5-dihydroxyphenyl)methanone;

(4-((4-Chlorophenyl)(pyridin-2-yl)methoxy)piperidin-1-yl)(2,5-dihydroxyphenyl)methanone;

N-((4-(4-Fluorobenzyl)morpholin-2-yl)methyl)-2,5-dihydroxybenzamide;

(2,5-Dihydroxyphenyl)(4-(5-fluorobenzo[d]isoxazol-3-yl)piperidin-1-yl)methanone;

N-(3,4-Dimethoxyphenethyl)-2,5-dihydroxybenzamide;

2,5-Dihydroxy-N-(2-(thiophen-2-yl)ethyl)benzamide; and 2,5-Dihydroxy-N-(2-oxotetrahydrothiophen-3-yl)benzamide, or a pharmaceutically acceptable salt or stereoisomer thereof.

3. A pharmaceutical composition comprising a compound according to claim 1, or a pharmaceutically acceptable salt or stereoisomer thereof.

4. A pharmaceutical composition comprising a compound according to claim 2, or a pharmaceutically acceptable salt or stereoisomer thereof.

5. A method for the treatment of a thrombotic disease, comprising:

administering to a subject in need thereof an effective amount of a compound of claim 1, or a pharmaceutically acceptable salt or stereoisomer thereof.

6. The method of claim 5, wherein the thrombotic disease is selected from the group consisting of pulmonary embolism, thrombotic phlebitis, deep vein thrombosis, portal thrombosis, angina pectoris, arteriosclerosis and cerebral infarction.

7. A method for the treatment of a thrombotic disease, comprising:

administering to a subject in need thereof an effective amount of a compound of claim 2, or a pharmaceutically acceptable salt or stereoisomer thereof.

8. The method of claim 7, wherein the thrombotic disease is selected from the group consisting of pulmonary embolism, thrombotic phlebitis, deep vein thrombosis, portal thrombosis, angina pectoris, arteriosclerosis and cerebral infarction.

\* \* \* \* \*